United States Patent
Cano Garcia et al.

(10) Patent No.: US 11,246,502 B2
(45) Date of Patent: Feb. 15, 2022

(54) MICROWAVE TOMOGRAPHY SYSTEM

(71) Applicant: Medical Wireless Sensing Ltd., London (GB)

(72) Inventors: Helena Cano Garcia, London (GB); Nadine Geddes, London (GB); Ioannis Gouzouasis, London (GB); Efthymios Kallos, London (GB); Panagiotis Kosmas, London (GB); George Palikaras, London (GB); Ioannis Sotiriou, London (GB); Anastasios Garetsos, Athens (GR); Georgios Stratakos, Athens (GR); Michail Gargalakos, Athens (GR); Constantinos Kakoyiannis, Athens (GR); Irene Karanasiou, Athens (GR); Maria Koutsoupidou, Athens (GR); Nikolaos Uzunoglu, Athens (GR)

(73) Assignee: Medical Wireless Sensing Ltd., London (GB)

(*) Notice: Subject to any disclaimer, the term of this patent is extended or adjusted under 35 U.S.C. 154(b) by 471 days.

(21) Appl. No.: 16/070,724

(22) PCT Filed: Jan. 17, 2017

(86) PCT No.: PCT/EP2017/050909
§ 371 (c)(1),
(2) Date: Jul. 17, 2018

(87) PCT Pub. No.: WO2017/125397
PCT Pub. Date: Jul. 27, 2017

(65) Prior Publication Data
US 2019/0021626 A1   Jan. 24, 2019

(30) Foreign Application Priority Data

Jan. 18, 2016 (GB) .................... 1600921

(51) Int. Cl.
*A61B 5/05* (2021.01)
*G06T 11/00* (2006.01)
(Continued)

(52) U.S. Cl.
CPC .......... *A61B 5/0507* (2013.01); *A61B 5/0042* (2013.01); *A61B 5/4064* (2013.01);
(Continued)

(58) Field of Classification Search
CPC .......... A61B 5/0507; A61B 2562/0228; A61B 2562/143; G06T 11/006; G06T 2207/10072
See application file for complete search history.

(56) References Cited

U.S. PATENT DOCUMENTS 5,588,032 A   12/1996   Johnson
6,144,701 A   11/2000   Chiang
(Continued)

FOREIGN PATENT DOCUMENTS

CN   204287070 U   4/2015
GB   2500719       10/2013
JP   2014-198067 A 10/2014

OTHER PUBLICATIONS

Liu et al., "Tunable meta-atom using liquid metal embedded in stretchable polymer" J. Appl. Phys. 118, 014504 (2015) (Year: 2015).*
(Continued)

*Primary Examiner* — Colin T. Sakamoto
(74) *Attorney, Agent, or Firm* — McDonnell Boehnen Hulbert & Berghoff LLP

(57) ABSTRACT

A novel medical imaging system that is based on radio-wave signals at microwave frequencies and has unique properties. The system can be used for various diagnostic applications
(Continued)

such as breast cancer detection, brain stroke detection, and assessment of internal bleeding (trauma emergencies).

26 Claims, 19 Drawing Sheets

(51) Int. Cl.
*A61B 5/0507* (2021.01)
*A61B 5/00* (2006.01)
*G02B 1/00* (2006.01)
*G01N 22/00* (2006.01)

(52) U.S. Cl.
CPC .......... *A61B 5/4312* (2013.01); *A61B 5/6834* (2013.01); *G02B 1/002* (2013.01); *G06T 11/006* (2013.01); *A61B 5/6803* (2013.01); *A61B 5/6814* (2013.01); *A61B 5/6823* (2013.01); *A61B 5/6824* (2013.01); *A61B 5/6828* (2013.01); *A61B 2560/0406* (2013.01); *A61B 2562/0228* (2013.01); *A61B 2562/046* (2013.01); *A61B 2562/143* (2013.01); *A61B 2562/168* (2013.01); *G01N 22/00* (2013.01); *G06T 2207/10072* (2013.01); *G06T 2207/20064* (2013.01); *G06T 2207/30016* (2013.01); *G06T 2207/30068* (2013.01); *G06T 2207/30096* (2013.01)

(56) References Cited

U.S. PATENT DOCUMENTS

| | | | | |
|---|---|---|---|---|
| 8,686,902 B2* | 4/2014 | Lopez | ................... | H01Q 1/243 343/700 MS |
| 9,504,404 B1* | 11/2016 | Shao | ................... | H01Q 21/064 |
| 2003/0018244 A1* | 1/2003 | Haddad | ................ | A61B 5/0507 600/371 |
| 2004/0077943 A1* | 4/2004 | Meaney | ................... | A61B 5/05 600/430 |
| 2005/0107693 A1 | 5/2005 | Fear | | |
| 2009/0009853 A1 | 1/2009 | Tonucci | | |
| 2012/0053445 A1 | 3/2012 | Turnquist et al. | | |
| 2013/0018591 A1* | 1/2013 | Grzegorczyk | ......... | G01N 22/00 702/19 |
| 2013/0225988 A1* | 8/2013 | Mahfouz | ................ | A61B 5/708 600/430 |
| 2013/0297223 A1 | 11/2013 | Fischer | | |
| 2014/0276031 A1 | 9/2014 | Lomnitz | | |
| 2014/0309528 A1 | 10/2014 | Lee et al. | | |
| 2014/0361769 A1 | 12/2014 | Hardie et al. | | |
| 2015/0045663 A1* | 2/2015 | Palikaras | ............. | A61B 5/0059 600/430 |

OTHER PUBLICATIONS

Mojabi et al., "Microwave Biomedical Imaging Using the Multiplicative Regularized Gauss-Newton Inversion" IEEE Antennas and Wireless Propagation Letters, vol. 8, 2009 p. 645-648 (Year: 2009).*
Ostadrahimi et al., "Enhancement of Gauss-Newton Inversion Method for Biological Tissue Imaging" IEEE Transactions on Microwave Theory and Techniques, vol. 61, No. 9, Sep. 2013 p. 3424-3434 (Year: 2013).*
International Search Report and Written Opinion of International Application No. PCT/EP2017/050909 dated Apr. 26, 2017, 13 pages.
Combined Search and Examination Report under Section 17 and 18(3) for Great Britain Application No. GB 1600921.9 dated Jun. 28, 2017, 7 pages.

* cited by examiner

MICROWAVE TOMOGRAPHY SYSTEM

This application is a national stage application under 35 U.S.C. § 371 of International Application No. PCT/EP2017/050909, filed Jan. 17, 2017, which claims priority to United Kingdom Patent Application No. 1600921.9, filed Jan. 18, 2016.

FIELD

The present disclosure relates to an antenna system, more specifically but not exclusively an antenna system for microwave tomography, and a microwave imaging system, more specifically but not exclusively a microwave tomography system. The present disclosure also relates to a metamaterial housing and a metamaterial device for imaging and tomography. The present disclosure further relates to a method of tomography and a method of coupling radiation into and out of a target for tomography. The present disclosure yet further relates to a wearable device for tomography.

BACKGROUND

Microwave imaging is the process of "seeing" the internal structure of an object by means of electromagnetic fields at microwave frequencies (300 MHz-30 GHz). The basic problem is illustrated in FIG. 1. A transmitter is used to illuminate the breast with microwaves, which travel through the breast and may be detected at receivers located on the opposite side of the breast. Alternatively, reflections may be recorded at the transmitting antenna. With a tumour present, waves traveling through the breast encounter a change in electrical properties, causing the incident wave to scatter. These scattering changes the amount of energy detected at the receivers and the transmitter, as shown in FIG. 1. Images are formed using information contained in the detected energies.

Specifically, FIG. 1 shows a transmitter 110 illuminating with microwaves a breast 130 having no tumours and a breast 140 having a tumour (shown as a solid square). Receivers 120 detect radiation passing through the breast 130, 140. As shown in the lower figure, reflections off the tumour may be received at the transmitter 110.

Microwave imaging for medical applications has been of interest for many years. Microwave images are maps of the electrical property distributions in the body—for example, the breast. The electrical properties of various tissues may be related to their physiological state. For example, the properties of tissues change with temperature.

One application of microwave imaging that has been proposed is monitoring hyperthermia, which is the application of heating tissue. In this case, changing electrical properties indicate the successful deposition of heat in the tissue of interest. Other changes in electrical properties may be caused by disease. There is some evidence of changes in the properties of cancerous tissues when compared to normal tissues. Cancer detection with microwave imaging is based on this contrast in electrical properties.

Another application of microwave imaging is as a post-trauma scanner. In this scenario, the system is used to image the internal tissues of a patient that has just suffered an accident. The system is located in an ambulance and can be placed around an arm, leg, head, or torso to generate an image and check for issues such as internal bleeding and/or broken bones.

Another application of the system is brain imaging, where an appropriately-shaped cup is placed around the head of a patient. The system then images the brain interior, providing information about blood clots and other abnormalities.

In the all these applications, the system can be portable and transported to different locations as needed.

Active Microwave Imaging (MWI) techniques for imaging internal body sections comprise mainly two categories: microwave tomography (MT) and ultrawideband (UWB) radar techniques. Microwave tomography aims to reconstruct the dielectric and conductive profiles of the breast while UWB MWI systems only identify the presence and location of strong scatterers in the breast based on their backscattered signals. UWB MWI systems use beamforming algorithms such as confocal microwave imaging (CMI) which can provide synthetic focusing of the scattered signals and are relatively simple. Another advantage of UWB MWI systems is their ability to acquire and process the scattering data in a very wide frequency band that can be up to several GHz. This procedure results in scattering images with good spatial resolution.

In contrast to radar-based approaches, the reconstruction algorithms of MT systems are based on iterative solutions of the nonlinear inverse electromagnetic (EM) scattering problem, and are conceptually challenging and computationally expensive. However, MT algorithms are powerful methods for diagnostics because they can reconstruct the full dielectric profile of the tissue interior. For cancer detection, MT imaging extracts tumour information via the scattering of microwaves from the different EM properties of the tumour compared to the surrounding tissues. The general operation principle is based on the placement of the object under measurement in a matching material medium (usually a water based material), which is irradiated by transmitting antennas while the scattered EM field is monitored by receiving antennas and evaluated by measurements from a vector network analyser (VNA), or custom-made transceivers. The receiving antennas usually perform scanning around the studied object and/or in conjunction with the movement/rotation of the studied object. Mathematical models and optimized evaluation algorithms are developed in conjunction with the use of powerful computers for the calculations. MT was not adequately developed until very recently because of the high cost of hardware and insufficient computing power.

The present disclosure aims to provide an improved microwave imaging system. In particular, the present disclosure aims to improve the coupling of microwave radiation into and out of the target.

SUMMARY

Aspects of an invention are defined in the appended independent claims.

There is provided an antenna mount comprising housing arranged to support an antenna array and delimit an imaging chamber. Notably, embodiments provide an arrangement of antennas in a semi-circular array around the breast and using a motorized system to scan the whole breast surface. The inventors have found that this method increases the resolution accuracy of the system as the antennas receive the scattered signals at any point along the rotation direction, when in most imaging systems that resolution is restricted by the separation between the antenna elements.

There is provided an improved microwave imaging system. Key features of the system include:
- A high-precision rotating mechanism for the imaging chamber-cup that adapts to the antenna transceivers and is based on a self-lubricant material (silicon or rubber) for ease of rotation.
- Rotating cup increases data acquisition locations
- Adjustable/Modular size cup (different sizes)/Adjustable Antenna mould depending on tissue sizes.
- Contact flange between the tissue and the mould assists the rotation in all cup sizes.
- Antennas are placed to the closest possible distance to the target tissue, thus small suction is created to adapt the target tissue to the cup mould.
- Small vacuum suction to form a maximum possible hemisphere within the antenna mould.
- Suction applicable at all sizes through the center of the cup
- The cup/system can be of spherical, cylindrical, or planar shapes
- The shape can be obtained via scan-design-print procedure, being totally customized and conformal to a particular body part (per user)
- Can be wrapped around different body parts: breast, arm, leg, head, torso
- The system can image (via dielectric profile reconstruction) tumours, bones, internal blood trauma regions, cartilage
- There can be a metamaterial film between the target tissue and the antenna
- The metamaterial film is disposable/replaceable based on the target tissue There is provided a metamaterial coupled to an internal wall of the imaging chamber. Embodiments use metallo-dielectric metamaterials in microwave imaging. Their unique properties can be tuned to result in a dramatic reduction of the unwanted skin reflections that plague virtually all microwave imaging systems built prior to the present disclosure.

Key features of the metamaterial include:
- Cylindrical/conformal metamaterial surface minimizes reflections and enhances signal penetration from the antennas into the target tissue;
- The metamaterial is wearable, i.e. it conforms to the shape of the target tissue without allowing air gaps.
- The metamaterial structure/stackup can be dielectric-metal or metal-dielectric-metal;
- Cross (Jerusalem)-like unit elements of novel design constitute embodiments of the metamaterial and have unique properties;
- The unit elements can be rectangular shape;
- The unit elements can be an overlaying cross and rectangle shape;
- One or two layer designs with suitable substrate materials ensure ease of use and fabrication;
- The metamaterial can have a dynamically tunable operating frequency;
- The metamaterial can be tunable by having a stretchable substrate;
- The metamaterial can be tunable by placing microfluidic channels over its unit cell elements; and
- The metamaterial array may comprise non-identical elements.

The system dramatically enhances sensitivity by using metamaterials as a matching medium. This is in contrast with conventional microwave imaging systems that typically require system components to be immersed in a matching liquid in order to maximize penetration through the tissue.

Rather than utilizing an expensive off-the-shelf vector network analyser to be included in the system for measuring the received signals, embodiments use a much simpler in-house analyser that measures the received signal amplitude and phase, which are the necessary RF parameters required to run the algorithmic processing. This significantly brings down the cost of the system, making it more affordable for easier penetration into the market.

Key features of the RF hardware include:
- An Ultra Wide Band super heterodyne receiver (0.8 GHz to 4 GHz) with a scanning capability to any frequency within this range;
- Very high interference rejection, implementing a combination of a high rejection tunable band pass pre-selection YIG filter and two surface acoustic wave band pass filters in series for the 1st and the 2nd IF stage respectively resulting in an 95 dB out of band rejection;
- The system could be connected with the use of an RF multiplexer with 16 antennas, allowing each one to transmit while the others receive. The receiver antennas can also be scanned independently one at a time. High isolation between the transmit and receive paths is achieved; and
- The system is controlled by microprocessor running at 80 MHz and a set of peripheral chips (EEPROM, FLASH, Communications transceiver, D/A converters, Real Time Clock, YIG Filter Driver etc.). Internally it has a rich set of peripherals, needed for the implementation of the motion functions and network communications.

The system utilises an imaging algorithm. Key features of the algorithm include:
- Iterative Gauss-Newton algorithm, which is able to use multiple frequency data (1.0-3.5 GHz) to improve resolution, and a two-step process to improve robustness;
- Low-frequency first-step reconstruction is used as the initial guess for the second multiple-frequency algorithm;
- Adaptive thresholding methods and wavelet basis expansions are used to improve the linear inversion at every step of the iterative algorithm;
- A GPU-based FDTD forward solver accelerates the inversion algorithm and enables two-dimensional images in real time as well as three-dimensional imaging offline and completed in less than 24 hours; and
- The algorithm can be dynamically adapted to account for different geometries/shapes of the cup/system, as provided by a scan-designed-print or similar procedure.

BRIEF DESCRIPTION OF THE DRAWINGS

Embodiments of the present disclosure will now be described with reference to the accompanying drawings in which.

In the figures, like reference numerals refer to like parts.

DETAILED DESCRIPTION OF EMBODIMENTS

Embodiments describe a system and component for imaging a human breast by way of example only. The present disclosure extends to imaging any biological target. The skilled person will readily understand how the physical form of components may be adapted for other biological targets. In embodiments, the biological target is a human breast, brain, torso, arm or leg.

The System

In overview, the present disclosure relates to a system which utilizes scattered microwaves between 800 MHz and 4 GHz to accurately reconstruct tissue distributions inside human bodies. The system consists of three main hardware components which, along with the appropriate software algorithms, provide the tissue distribution and dielectric/conductivity profile. A system overview is shown in FIG. 2.

The three main components of the system are the microwave scanner which has the combination of non-ionising low-power microwave transceiver and the uniquely designed antenna array allowing efficient transmission and signal capturing; a wearable medium that allows penetration of low power microwaves through skin; and a unique interpretative algorithm, which translates and analyses captured signals into images.

Figure 1:
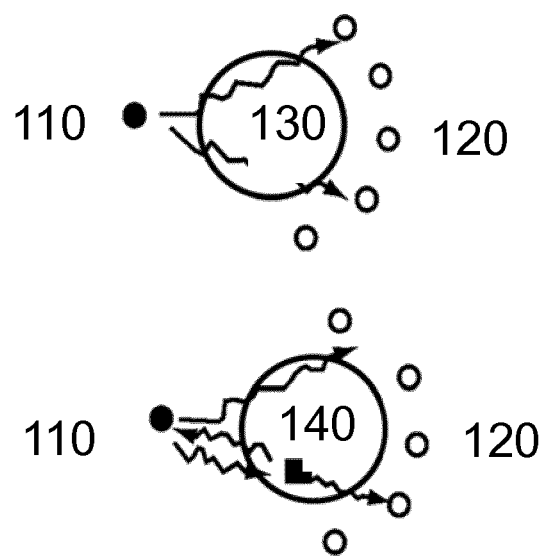
FIG. 1 shows principles of microwave imaging.
Figure 2:
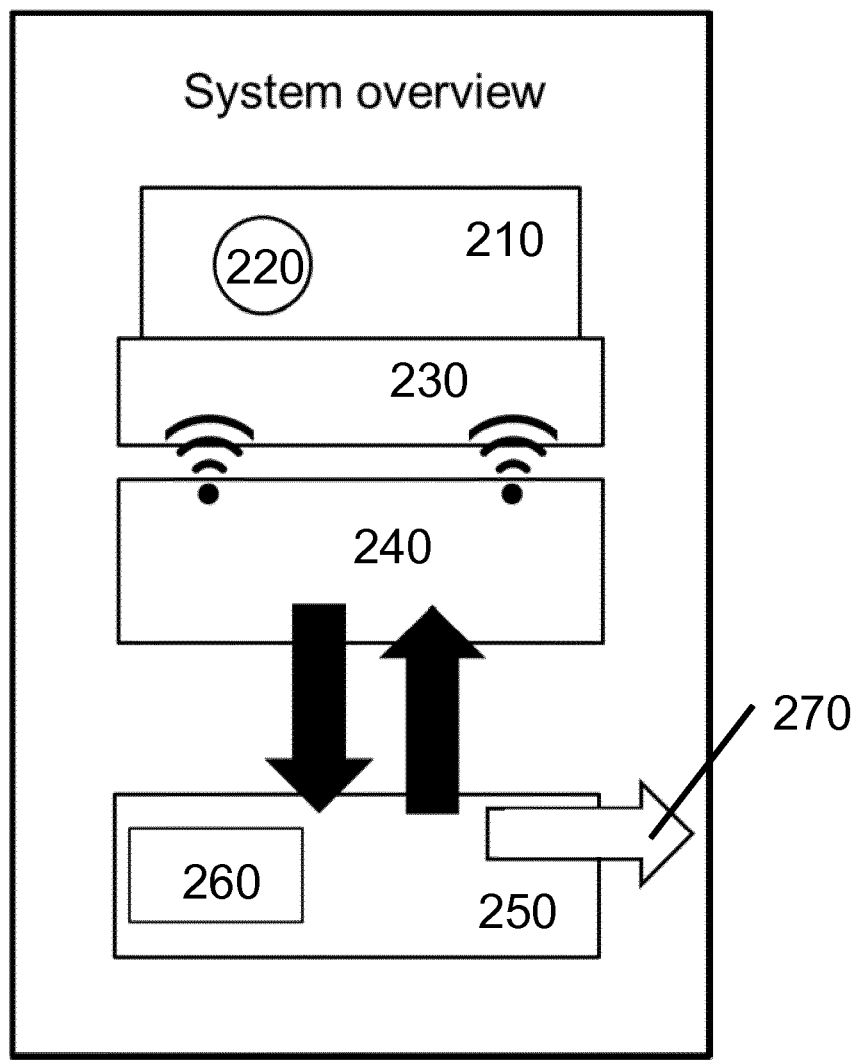
FIG. 2 is an overview of system components.

Specifically, FIG. 2 shows a body 210 comprising tissue 220 wherein the body is in physical contact with a matching medium 230. RF antennas 240 irradiate body 210 via the matching medium 230. The RF antennas are in two-way communication with an electronic processing unit 250 comprising algorithmic processing 260. The electronic processing unit 250 is arranged to output a diagnosis 270.

The wearable medium is a "metamaterial" placed between the system antennas and the target tissue. That is, the metamaterial is wearable. It is a removable component that may be removed or replaced for hygienic purposes. The metamaterial may be a film. In embodiments, a different film is applied for different patients and/or body parts. The film may be a disposable and in certain cases the overall system is unable to produce accurate images without it, because not enough energy reaches the receiving antennas and the signal-to-noise ratio is very low.

Figure 3:
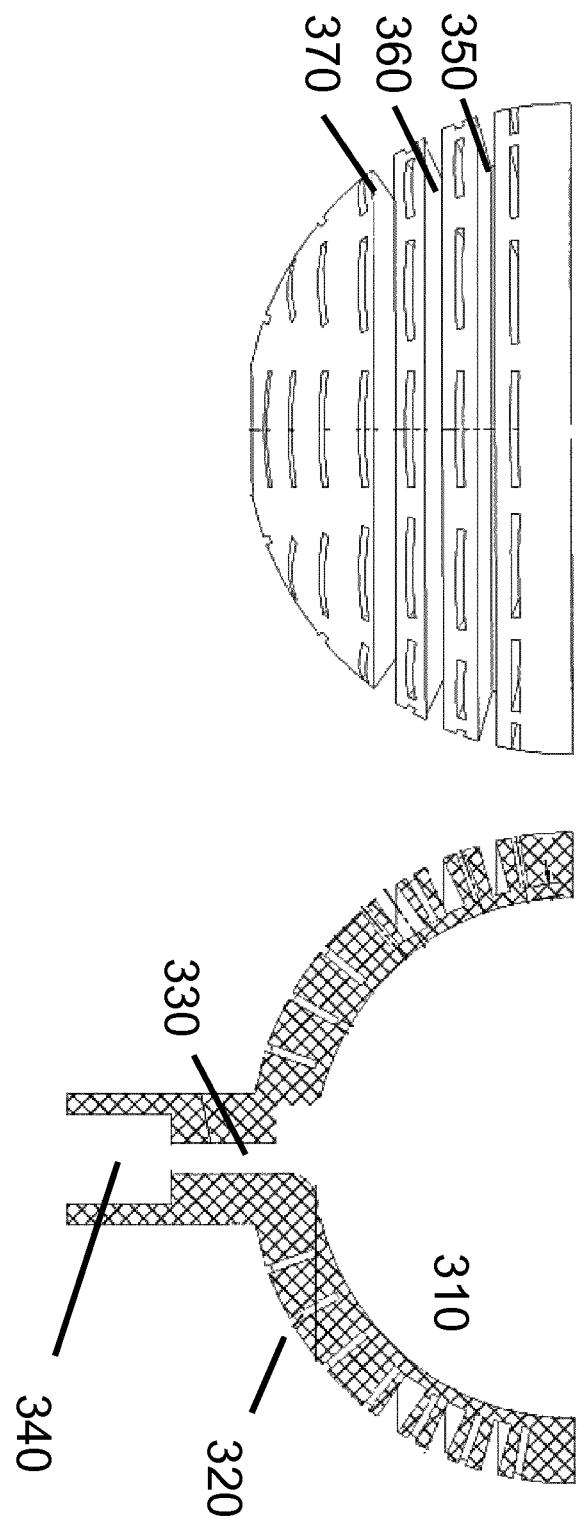
FIG. 3 shows a tissue cup in accordance with embodiments.

For the case of imaging a breast or brain to detect tissues, the chamber—cup can be a hemisphere, as shown in FIG. 3; all the elements of this array are slotted in this hemisphere. Each antenna in the array is equidistant from the center of the hemisphere and is placed in the slots around at the same azimuth of the hemisphere; a circular pattern antenna array is finalized in a tomographic orientation, while tangent and perpendicular to the breast cup prototype. The arrays of the cup sum up to seven layers that are shown in FIG. 3. The radiation of all antennas is facing towards the center of the breast cup gathering information from the maximum possible positions. One more function that is determined is the rotation of the cup and at the same time keeping the antennas fixed and again tangent on the cup.

The section view of FIG. 3 reveals the slots were the antennas are to be housed while the system is rotating 180°. Three sliding antenna slots are used to freely rotate the system while the antennas are fixed in a certain position. This will be a new measurement procedure that will generate data throughout the dimension of the perimeter at a given level.

Specifically, FIG. 3 shows two views of a tissue cup arranged to receive a breast phantom 310. The tissue cup comprises antenna slots 320 each arranged to receive an antenna. A path 330 into the imaging chamber is provided to stabilise the breast phantom 310. A hexagon stepper 340 towards a stepper motor, for rotating the tissue cup, is provided. A first sliding slot 350 for stable antenna and second wider slot 360 and third wider slot 370 are provided. Slots 350, 360 and 370 are each arranged to receive an antenna. The cup is configured such that it can freely move with the antennas simply sliding around it. Advantageously, this allows differently shaped antennas to be used, unlike the other slots which are configured to receive an antenna of particular width only. By way of example only, the tissue cup may have an internal diameter of 200 mm and the imaging chamber may have a depth of 100 mm.

It may therefore be understood that there is provided an antenna system comprising: an antenna mount comprising a first housing at least partially defining an imaging chamber for receiving a biological target, wherein the first housing comprises a first plurality of antenna sockets each arranged to receive a respective antenna and direct the antenna into the imaging chamber; and a metamaterial coupled to the internal wall of the imaging chamber.

The imaging chamber provides an imaging volume for the biological target such as a human breast. The first housing therefore delineates or delimits the imaging chamber/volume. The first housing surrounds the imaging chamber/volume.

The antenna sockets are fixtures or mounts or receiving portions each configured to receive an antenna. The antenna receiving portions are arranged to closely-couple each antenna with the imaging chamber and therefore the biological target. The first housing may be considered an antenna mount—that is, a mount for a plurality of antennas. The first housing is arranged to receive or accommodate the metamaterial.

Anthropometrics and ergonomic sitting posture of the target user create a relaxed and user centered design solution. Moreover, tissue motion of the imaged object during measurements is a problem. In medical imaging, patients move because they breathe, they grow frustrated or nervous, have some medical condition, etc. Motion causes image blurring and, as a consequence, reduces the sensitivity and the resolution of the imaging procedure. In accordance with the present disclosure, motion is reduced by 1) constraining the body part between plates, hemispherical cups, etc. and 2) using prone positioning (lying face down with the abdomen against the examination table) of the patient as in MRI breast examination. The latter helps to limit motion due to breathing—the front chest wall is pressed against the examination table and remains stationary while it is the back that moves.

Embodiments provide:
1. Ergonomics—Comfort;
2. Adjustable Antenna mould depending on Breast sizes;
3. Antenna mould rotation;
4. Metamaterial on breast (between breast and antennas);
5. Limited movement for the cables connected to the antennas;
6. Programmable chair positions;
7. Electro-Hydraulic Movement-Foot multifunction control; and
8. Small pump for breast suction (Small vacuum suction) to form a maximum possible hemisphere within the antenna cup—see FIG. 4.

Figure 4A:
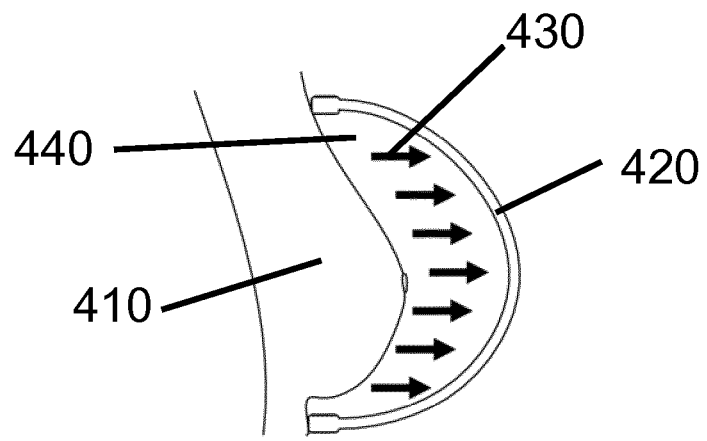
FIG. 4a shows a suction system of embodiments.
Figures 4B, 4C:
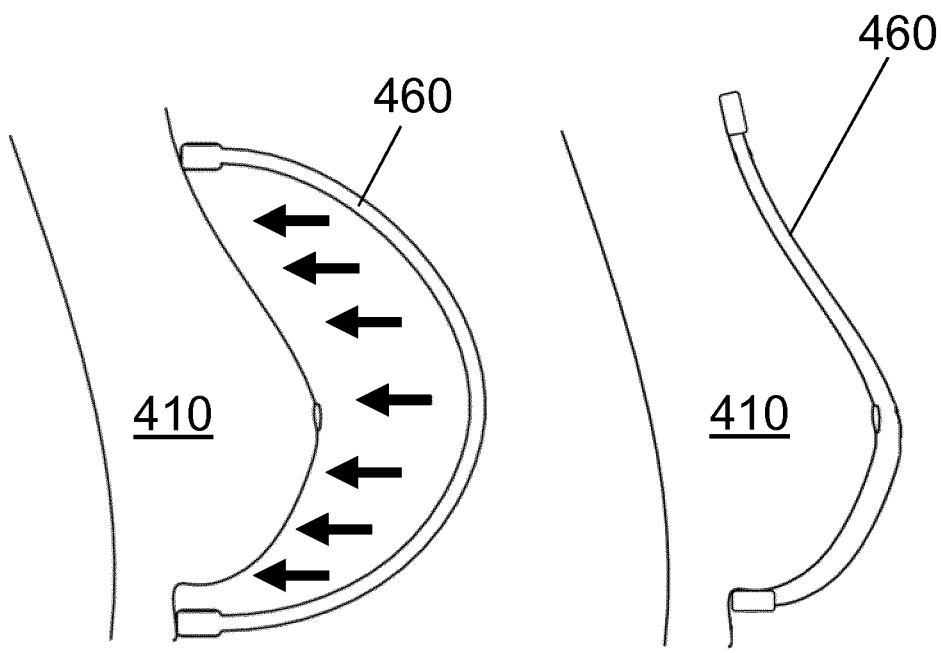
FIGS. 4b and 4c shows the concept of wearable metamaterial that conforms to the shape of the biological target wherein there is shown a breast, a metamaterial at a distance (left) and applied onto tissue (right)
Figure 5:
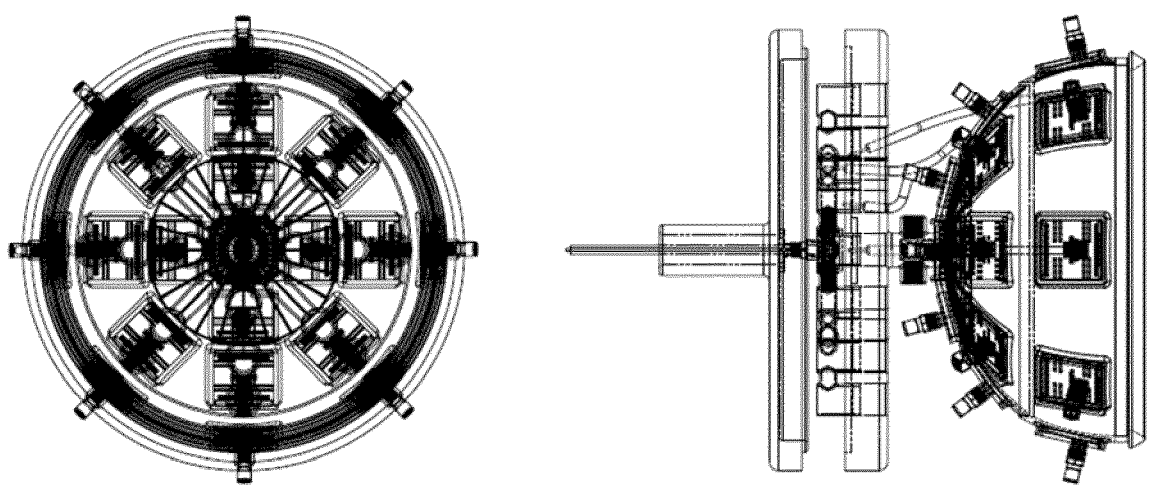
FIG. 5 is a detailed drawing of an embodiment for imaging a breast.

Specifically, FIG. 4a shows a small breast 410 and an adjustable antenna mould 420 arranged to remove air 430 from the imaging chamber 440. FIGS. 4b and 4c show the concept of a wearable metameterial 460 conformable to the shape of a breast, in accordance with embodiments. FIG. 5 shows more detailed drawings of a breast cup design in accordance with embodiments.

It may therefore be understood that, in embodiments, the first housing is a substantially spherical, hemispherical or parallelepiped shell and the imaging chamber is the internal volume of the shell. The first housing may be arranged to rotate around the imaging chamber.

Embodiments comprise a second housing at least partially defining the imaging chamber, wherein the second housing comprises a second plurality of antenna sockets each arranged to receive a respective antenna and direct the antenna into the imaging chamber, wherein the second housing is arranged to rotate around the imaging chamber. In these embodiments, the first housing and second housing collectively form a substantially spherical, hemispherical or planar shell and the imaging chamber is the internal volume of the shell. The second housing may be rotatably-coupled to the first housing.

Further embodiments comprise a third housing at least partially defining the imaging chamber, wherein the third housing comprises a third plurality of antenna sockets each arranged to receive a respective antenna and direct the antenna into the imaging chamber, wherein the third housing is arranged to rotate around the imaging chamber. In these embodiments, the first housing, second housing and third housing collectively form a substantially spherical, hemispherical or planar shell and the imaging chamber is the internal volume of the shell. The third housing may be rotatably-coupled to the second housing.

In embodiments, each housing comprises suction holes arranged to couple with a suction system for removing air from the imaging chamber. It may be said that the suction holes allow for air to be at least partially evacuated from the imaging chamber. The metamaterial may be perforated to facilitate the same.

In embodiments, there is provided a method of operating the system comprising the following ordered steps:

1. Before starting the measurement, a special ring with an elastic membrane of Metamaterial is attached on the tissue, helping microwaves overcome the skin barrier—this will be working as the matching layer for the signal to penetrate the skin barrier;
2. In embodiments, the is provided in 3 basic sizes scaling from Small to Large in diameter and depth and all three will be perforated to engage with the suction system;
3. Test takers will bend down on their knees and the seat will be adjusted—leaning forward will locate the breast to the proper measuring position;
4. Qualified personnel at this point will be responsible of aligning the antenna cup with the breast for perfect attachment;
5. The Metamaterial ring will be engaged on the top of the hemispherical measuring antenna cup depending on the size of ring used initially;
6. Suction system will apply small scale vacuum suction to the breast. The suction will be applied for the breast expansion towards the cup wall and furthermore to the antennas—this will minimize the measuring errors and achieving the best possible measurement;
7. When the measurement starts, the antenna cup will be rotating in an angle of 180°, producing a 3D breast image of the breast;
8. Once the measurement is finished, vacuum pressure is removed from the breast and finally disengaging the metamaterial ring from the antenna cup; and
9. The Metamaterial ring may be disposed and may be specially recycled.

Figure 6:
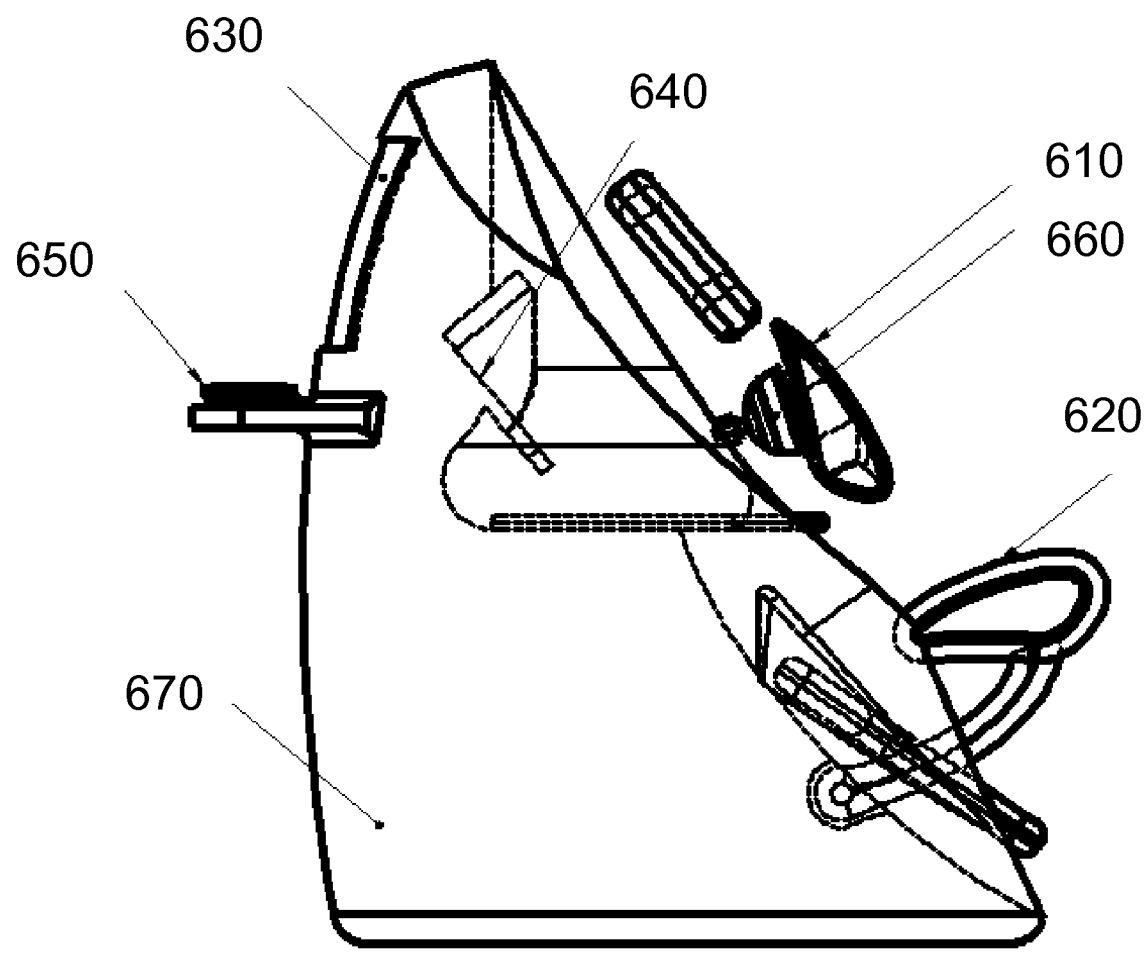
FIG. 6 shows an inclined chair system comprising embodiments of the present disclosure.

FIG. 6 shows a detailed drawing of an inclined chair in accordance with embodiments. Specifically, FIG. 6 shows a chest cushion 610, a seat 620, a screen for the operator 630, an optional inner screen for the test taker 640, a control panel 650, a breast cup 660 and an outer body 670 including microwave electronics-cpu-pneumatic pump etc.

Figure 7:
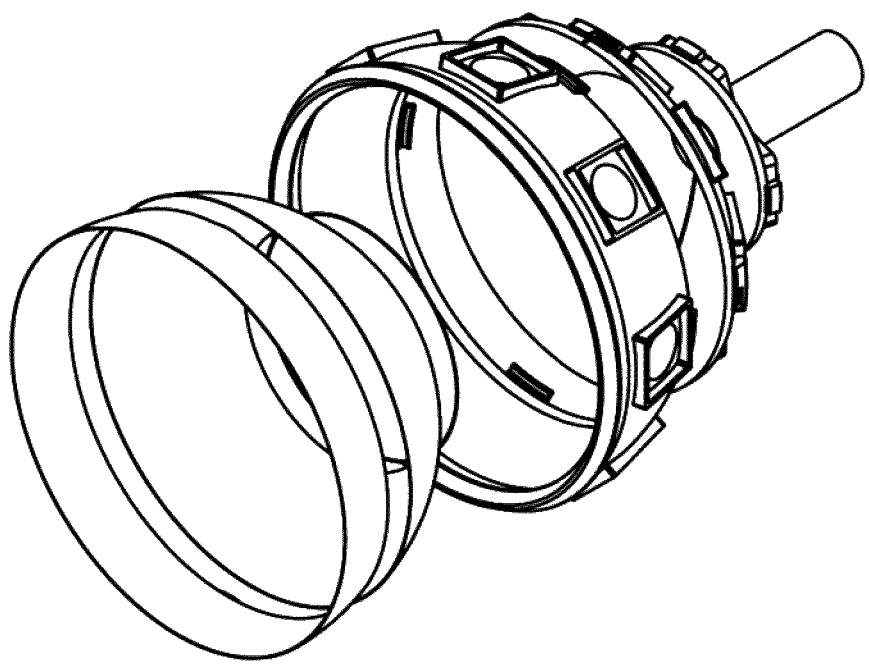
FIG. 7 shows an embodiment comprising a hemispherical cup with metamaterial layers.
Figure 7:
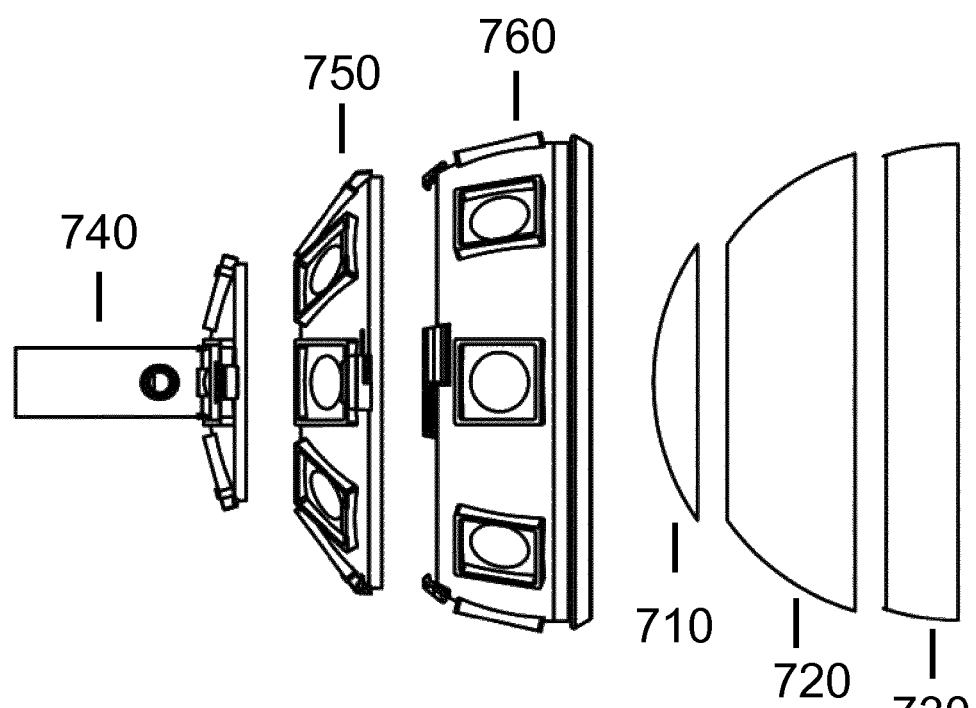

FIG. 7 shows an embodiment comprising a hemispherical cup design with metamaterial layers. Specifically, FIG. 7 shows a first housing 740, second housing 750 and third housing 760 respectively arranged to receive first 710, second 720 and third 730 metamaterials.

Figure 8:
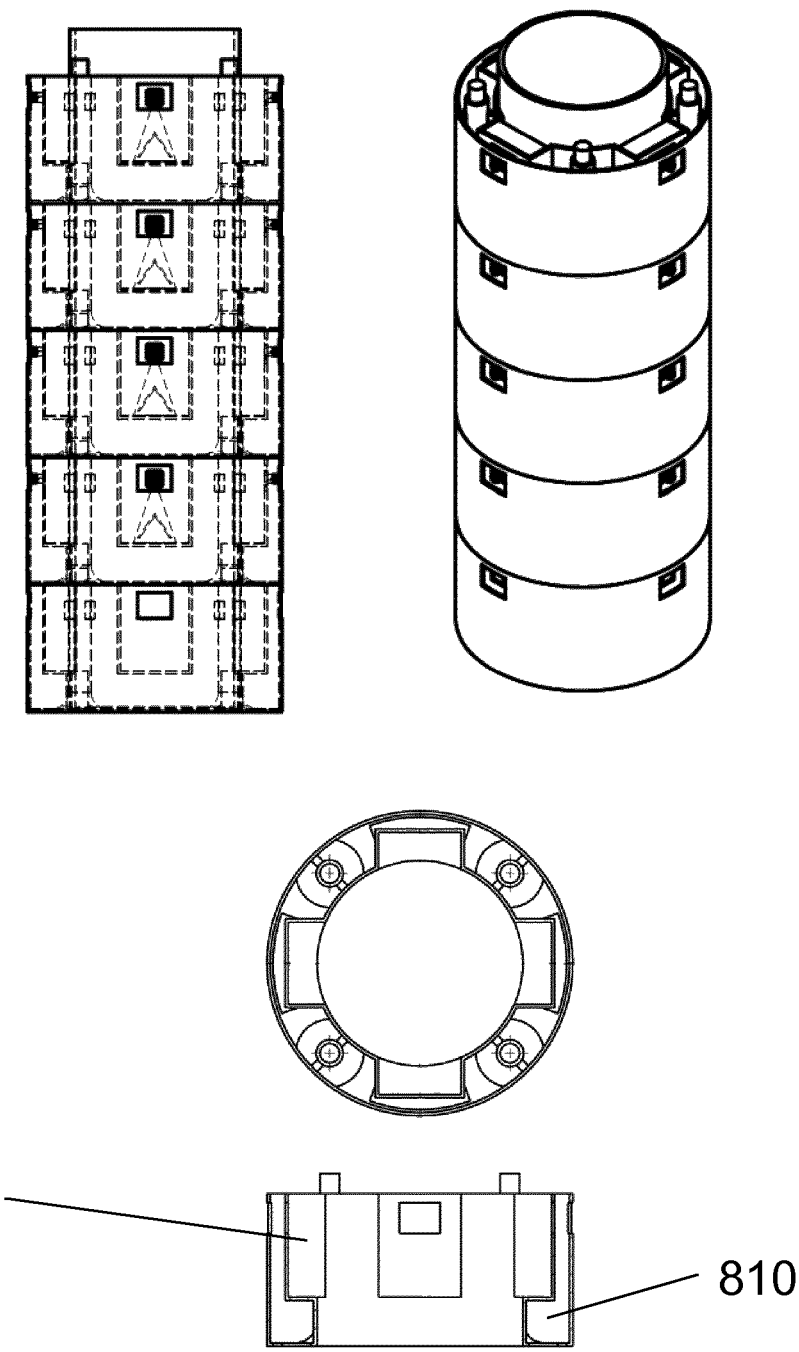
FIG. 8 shows an embodiment comprising a cylindrical configuration.

FIG. 8 shows an embodiment comprising a cylindrical setup design. Specifically, FIG. 8 shows that the system comprises a plurality of absorber housings 820 each arranged to respectively receive an absorber 810 which surrounds the antennas to prevent interference therebetween.

The cylindrical setup is a system constructed to test the wave transmission on the acrylic cylindrical tank (100 mm OD×94 mm ID×495 mm). The tank creates a volume of approximately 3.5 litres. This is filled with the Object Under Test (e.g. phantom or body part such as arm or leg).

In embodiments, the operating antennas are provided in a 5×5 pattern, creating 25 transmitting and receiving points. However, it may be understood that any number of operating antenna may be used in any preferred configuration. In embodiments, the hollow designed part (section A-A) is filled with absorbing material (4) to stop travelling waves from interfering with the rest of the receivers. In embodiments, the construction is modular so it can accommodate at any time extra antennas in the given cylindrical shape.

3D scanning and printing technologies have opened up the capabilities for customization in the medical field. Using proprietary, biocompatible, and drug-contact materials, parts can be produced that are perfectly suited for a particular individual. The conformal geometries described above and depicted in the accompanying drawings are technological advancements capable of providing new tools for imaging techniques.

Embodiments provide:

3D scanning of a part of the body to recognize the body parts geometries;

3D model produced and checked through CAD software, fixing the surfaces and moreover;

Embedding the geometry coordinates to dynamically interchange/alternate the algorithm to enhance the image resolution; and 3D printing such custom shapes for better diagnosis.

Embodiments utilising 3D printing enable mass customization. That is, multiple individualized items are produced simultaneously, saving time and energy while improving manufacturing efficiency. In embodiments, the consumables for effective imaging systems are 3D printed. In embodiments, patient 3D scanning, CT or MRI scans are used to create STL files to print solid 3D models, which are then be used as templates for consumable parts. In conjunction with a flexible metamaterial, this allows the system to compensate for different sizes and shapes of biological target. Specifically, information regarding the precision positioning of each antenna during a scan can be used to ensure an accurate reconstruction of the target is formed by the algorithm. In embodiments, the antenna positional information is provided as an input to the algorithm.

As trauma is the leading cause of death for persons aged 1 to 44, a vital part of trauma care is recognizing and treating signs and symptoms of bleeding. Profuse bleeding is life threatening requiring immediate attention. Embodiments provide a microwave imaging head cap arranged to accommodate a variety of antennas in different patterns aiming in quickly recognizing internal bleeding in trauma.

Figure 9:
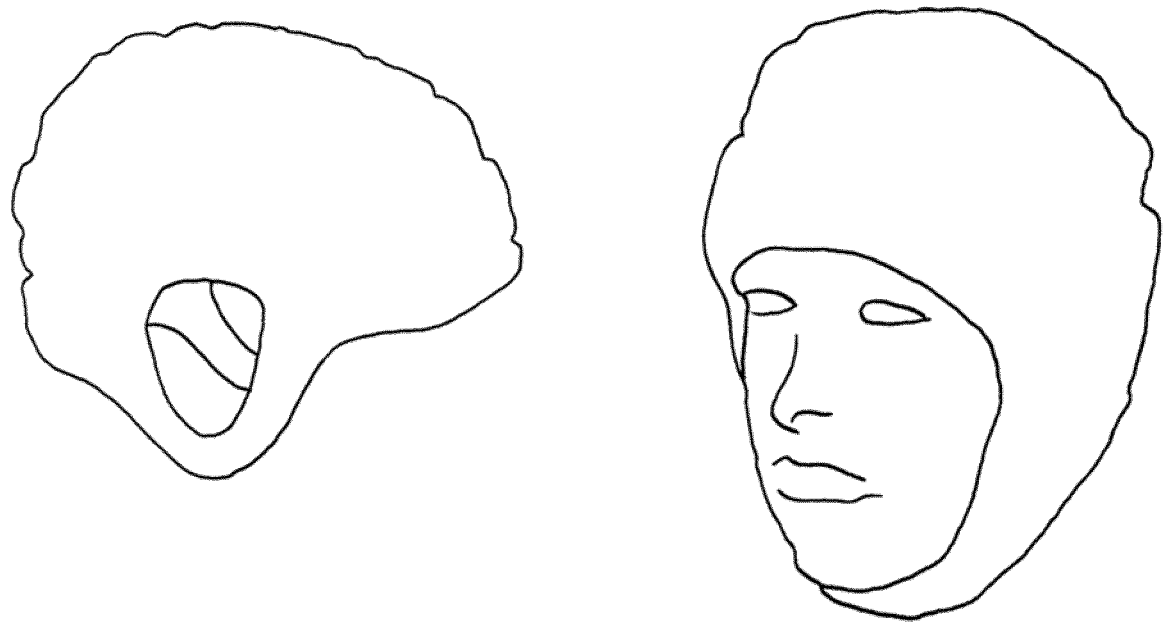
FIG. 9 shows a head cup embodiment.
Figure 10:
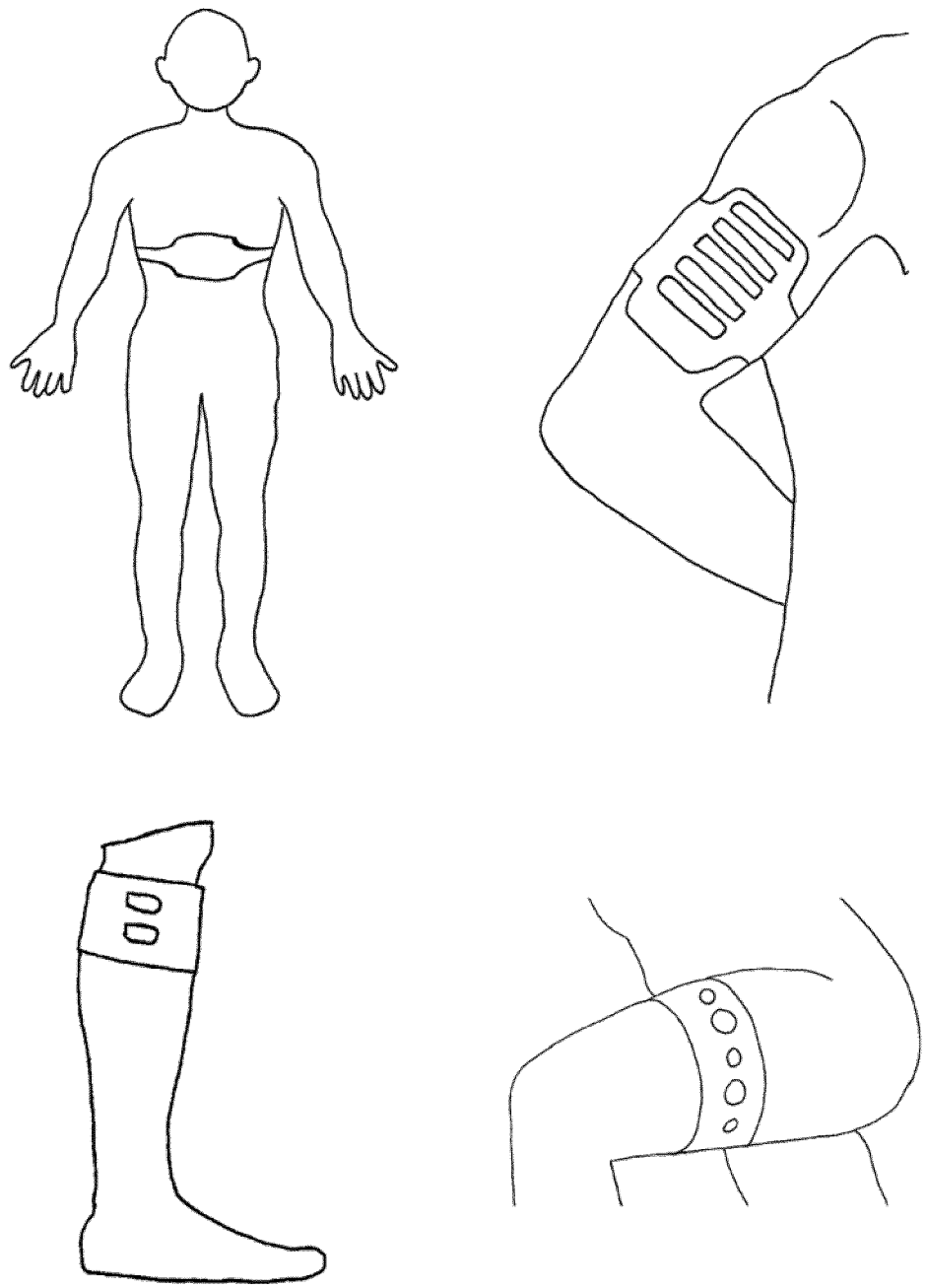
FIG. 10 shows further wearable embodiments.

FIG. 9 shows a head cap in accordance with embodiments. FIG. 10 shows other embodiments comprising wearable imaging devices on the (a) torso, (b) arm, (c) knee and (d) leg.

It may therefore be understood that in embodiments, the first housing is non-rigid so as to be conformable to the shape of the biological target. Likewise, in embodiments, the metamaterial is non-rigid so as to substantially conform to the shape of the internal wall of the imaging chamber.

There is provided an antenna mount comprising a first housing at least partially defining an imaging chamber for receiving a biological target, wherein the first housing comprises a first plurality of antenna sockets each arranged to receive a respective antenna and direct the antenna into the imaging chamber, wherein the first housing is arranged to rotate around the imaging chamber. Optionally, the antenna mount may further comprise a second housing arranged to independently rotate around the imaging chamber.

Antenna Array

A core component of the system is the microwave antenna array. A sufficient number of transmitters and receivers are placed on a region—for example, a semi-circular/hemispherical region—that may completely surround the object under investigation, optionally, with appropriate motorized rotation movements, in order to characterize its properties by measuring the scattered fields. In embodiments, the body part is placed in a cup of modifiable size and shape to suit the patient.

In embodiments, each sensor is alternatively activated as a transmitter and the scattered signal at the rest of the sensors is received, thus allowing the use of information (amplitude and phase) from all directions in the reconstruction procedure. This is the so-called multistatic approach, where a real aperture array is used for data collection. This approach exploits multiple received signals that propagate via different paths accumulating more information about the tumour. This multiple angle view can be enhanced by the design and implementation of multiple polarization antennas.

Desired characteristics of these antennas include their ability to operate in a wide frequency band, compact size, dual independent linear polarization, isolation from nearby interference, and high radiation efficiency. Embodiments use dipole antennas, dielectric resonator antennas, patch antennas, slot antennas, and/or Vivaldi antennas. Other embodiments use MEMS-steerable antennas to enhance the scanning at different angles via rotation and could generate two independent linear polarizations which resulted in increasing the possibility of imaging the tissue interior accurately. A wideband pulse signal with frequency spectrum between 800 MHz to 4 GHz is proposed as the illuminating signal, since it provides enhanced image resolution when compared to single-frequency reconstructions, and hence obtains an image with fewer artifacts that could be interpreted as false positive detections.

Metamaterial Matching Medium

In accordance with the present disclosure, a Metamaterial matching medium is placed between the antenna array and the human body. The purpose of this component is to maximize the penetration of the microwave radiation into the tissue region, which is normally significantly reflected from the skin tissue as it enters from the surrounding air environment. That is, in embodiments, the metamaterial is arranged to impedance match with the biological target. Embodiments use metallo-dielectric materials.

Figure 11:
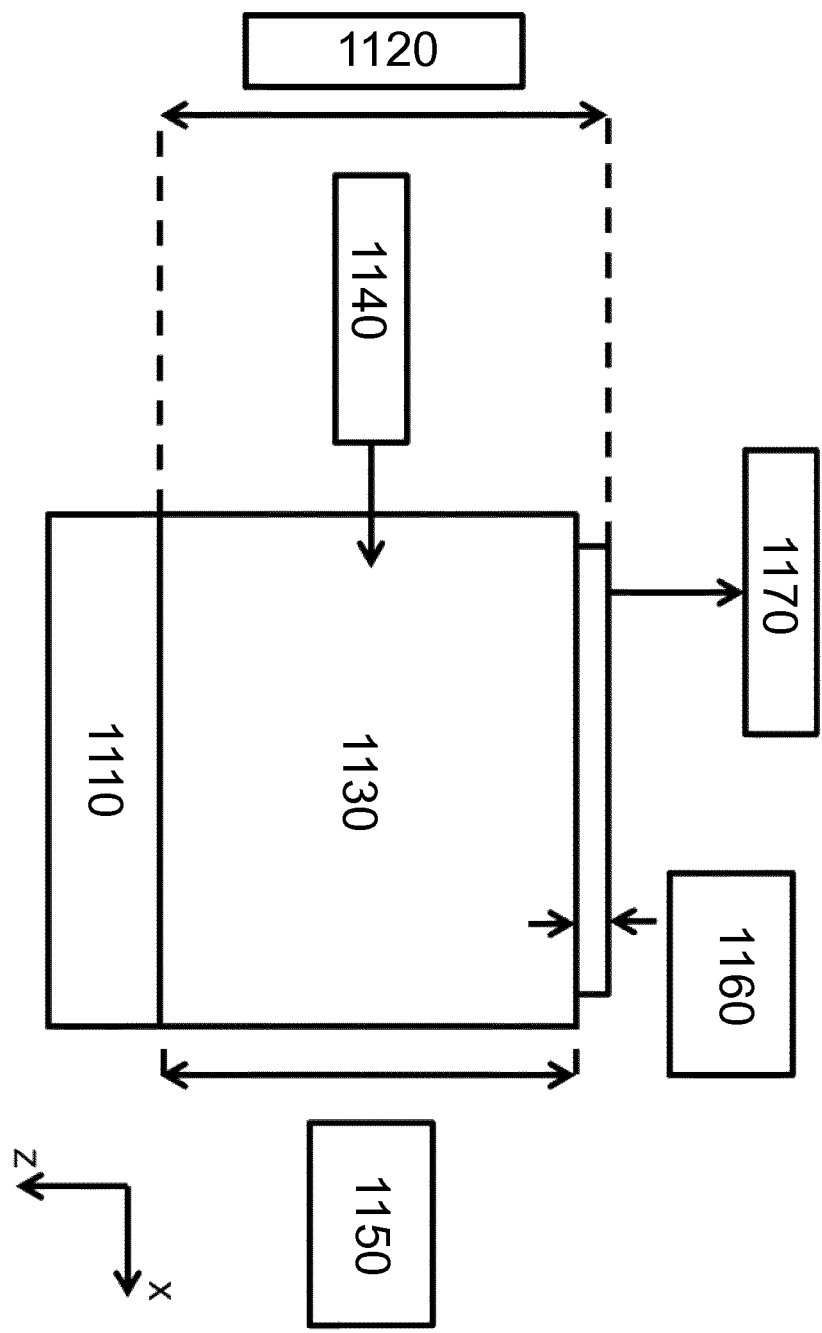
FIG. 11 is a schematic representation of a metamaterial in accordance with embodiments.

A metamaterial is an artificial structure that can give certain properties to EM radiation that are not possible to find in nature. This structure may consist of two layers as shown in FIG. 11. Reading bottom up, the first layer is a dielectric material of specific dimensions and EM properties. The second layer is copper, which is printed on top of the dielectric with a specific fabrication process and is facing the impinging EM wave. The combination of both layers affects the wave in a way that minimizes the reflection from the breast skin tissue behind the metamaterial. In embodiments, the metamaterial comprises at least one metamaterial layer arranged to line the internal wall of the imaging chamber.

FIG. 11 is a schematic representation of the metamaterial (side view). The copper layer faces the EM wave and the dielectric substrate lies on the human breast tissue. Specifically, FIG. 11 shows breast skin tissue 1110 in physical contact with a dielectric substrate 1130 of metamaterial 1120. The dielectric substrate 1130 has a dielectric thickness 1150. Metamaterial 1120 further comprises a copper layer 1160 forming a front layer 1170, wherein the copper layer 1160 comprises a plurality of "meta-elements" facing the EM radiation.

In embodiments, the thickness of the metamaterial is sub-wavelength, i.e. less than the wavelength of the highest frequency of operation. The frequencies of operation are within 1-4 GHz. That is, in embodiments, each respective antenna is a radio-frequency antenna arranged to emit or receive a microwave signal and each metamaterial layer has at least one dimension less than the wavelength of the microwave signal. In embodiments, at least one dimension includes the thickness of the metamaterial layer.

Figure 12:
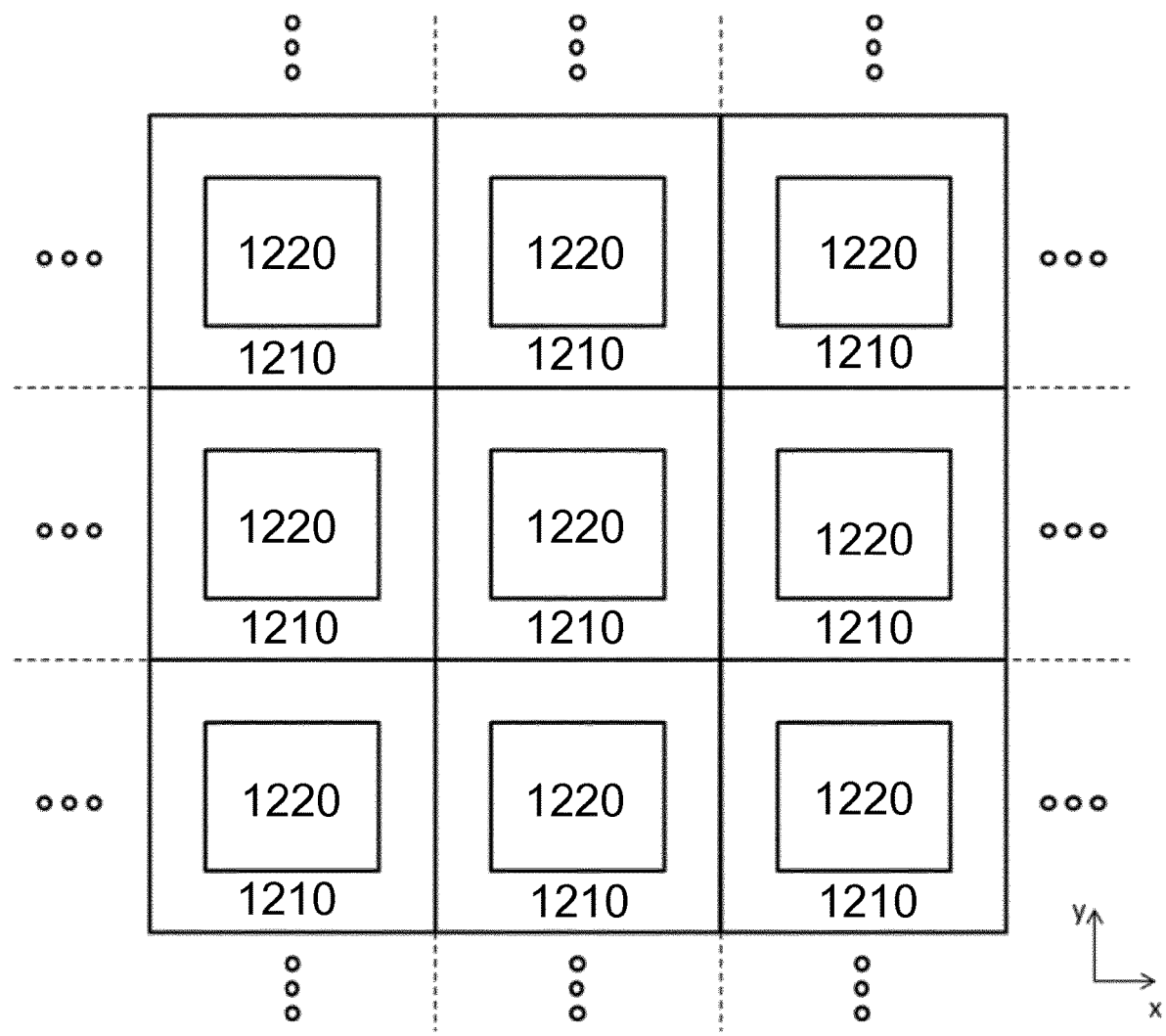
FIG. 12 shows a metamaterial in accordance with embodiments.

The design of the copper layer is repeated on the surface of the dielectric in regular intervals, forming a pattern. Hence, the pattern consists of multiples of single elements as shown in FIG. 12. FIG. 12 shows that the metamaterial is a repetitive pattern of a single dielectric/copper element in both x and y axes. The design of the copper is specific for each frequency of operation. Specifically, FIG. 12 shows a regular array of quadrangular elements 1220 (e.g. copper elements) arranged on a substrate formed of material 1220 (e.g. dielectric).

Normally, a specific copper design is tied to a specific operating frequency. However, the metamaterial can become tunable in order to perform in a range of frequencies. That is, in embodiments, the metamaterial has a dynamically tunable operating frequency. The tunability can be achieved by means of mechanical stretching or microfluidics. In the first case, a mechanical force is applied on the metamaterial which changes its physical dimensions according to the desired frequency. In the second case, a liquid can be infused in the structure and become either part of the copper layer or the substrate. The liquid can be metal or other material and its presence alters the electromagnetic characteristics of the structure, leading to a shift in frequency resonance.

That is, further to static metamaterial designs, in embodiments the metamaterial elements can be dynamically tunable with frequency. This means that the frequency band of operation of the metamaterial can be actively tuned externally and at will.

There are three main types of tunable metamaterials of interest: voltage-tunable MEMS, microfluidic channels, and optically tunable.

In the voltage-tunable metamaterial case, a voltage-controlled tuning element such as MEMS (microelectromechanical systems) varactor is used. By applying a voltage across each metamaterial element equipped with a varactor, the distance (height) can be adjusted for example through the electrostatic force attraction. By changing this distance between two layers of metamaterials, the resonance frequency is also altered through the change in the capacitance of the element.

In the microfluidic channel metamaterial case, a small hollow tube runs above or below each metamaterial element. The tube is at will filled with a liquid, typically water, and can be switched on and off. When the tube is filled with water, the permittivity in the vicinity of the metamaterial elements is altered (it becomes higher than air or a dielectric), and thus the overall resonance frequency can be tuned.

Figure 13:
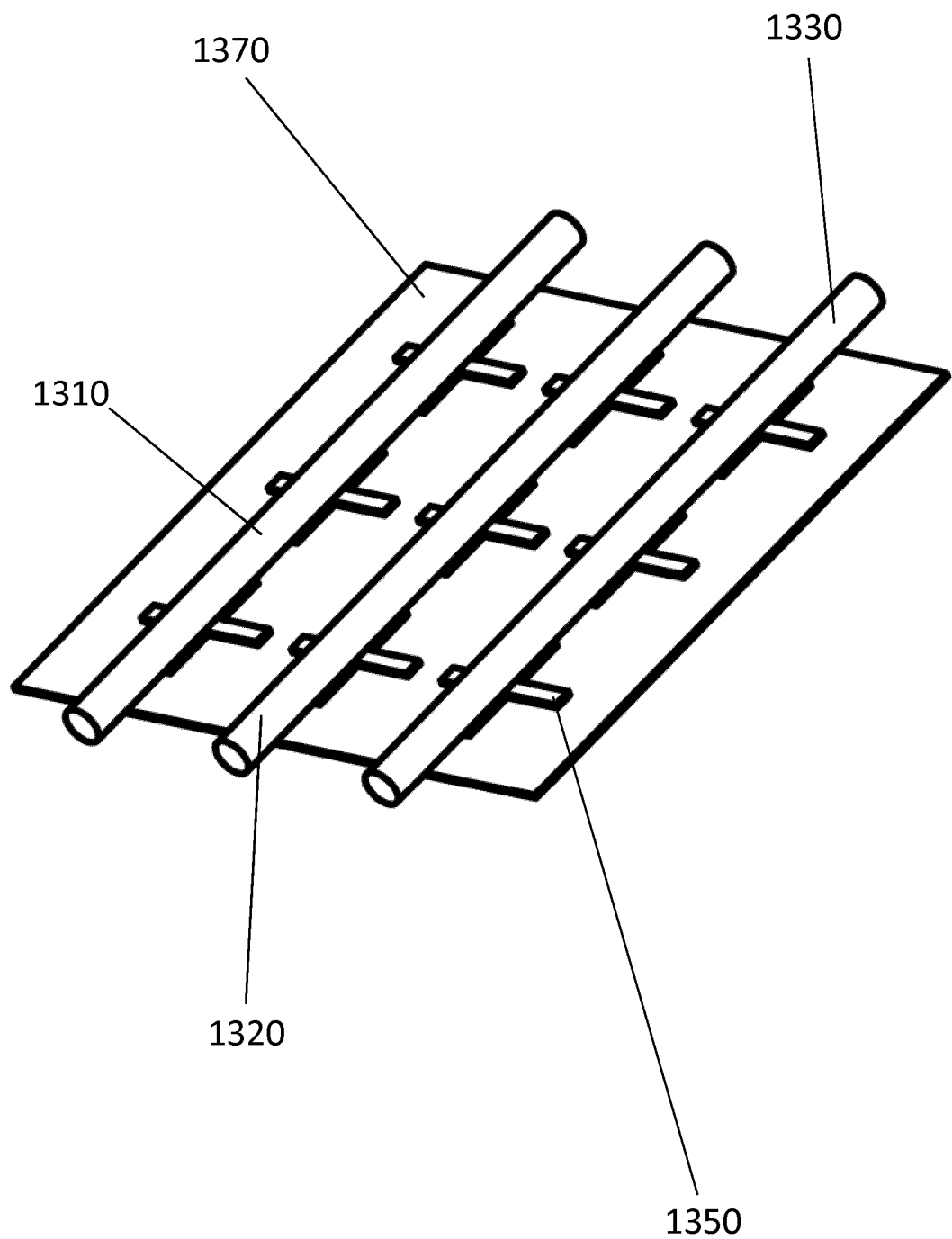
FIG. 13 shows the principle of a tunable metamaterial via microfluidic channels placed in the proximity of the metamaterial elements.

FIG. 13 shows a plurality of metamaterial elements 1350 provided on a substrate 1370. FIG. 13 further shows a first microfluidic channel 1310 in contact with a first plurality of metamaterial elements, a second microfluidic channel 1320 in contact with a second plurality of metamaterial elements and a third microfluidic channel 1330 in contact with a first plurality of metamaterial elements.

In the optically tunable case, the metamaterial element comprises partly of a photo sensitive material, such as a photoconducting semiconductor. The photo sensitive material has a permittivity and conductivity value that can be altered by the incidence of light upon it. For example, an 800 nm pump diode light source can be used. This means that the material can be at will turned conductive, and thus current can flow across it. As a result, the metamaterial shape can be altered as in the latter case the conductive (metallic) region can be extended. This affects the overall metamaterial shape, and thus tunes its resonant frequency. For example, if the metamaterial element is a mostly metallic cross, and the edges of the cross are constructed from the photoconductive material, then by switching the pump light on and off the length of the cross edges will be tuned (shorter or longer), as the photoconductive material becomes conductive or not.

Figure 14:
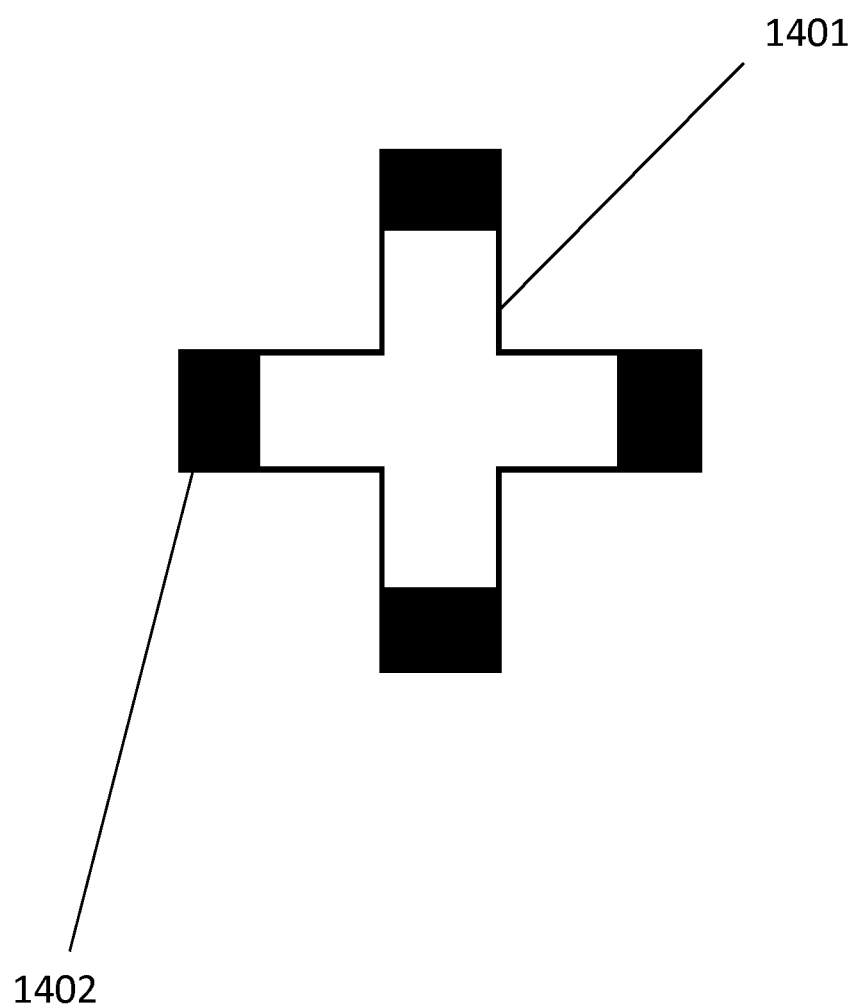
FIG. 14 shows a photoconductive metamaterial element, in accordance with embodiments, wherein the light area is a conventional metal, while the dark areas represent photoconductive material.

FIG. 14 shows a metamaterial element 1401 and a plurality of photoconducting materials 1402 configured to provide this tunability.

It may therefore be understood that, in embodiments, the system further comprises a microfluidic channel in contact with second components of the periodic array of second components. In embodiments, the system further comprises a microfluidic controller arranged to selectively supply fluid to second components of the periodic array of second components, optionally, wherein the fluid is water. In other embodiments, the metamaterial comprises a photoconducting material or material having light-sensitive permittivity.

In all embodiments, the presence of the metamaterial in front of the breast skin tissue has the effect of increasing the energy penetration and higher power can be received at the other side of the tissue. This leads to increased SNR of the received signal, which improves the performance of the software algorithm. Therefore, the metamaterial becomes an essential part of the system such that it may not work without it. The metamaterial may be considered a membrane or film.

In embodiments, a copper design is printed on a dielectric whose shape conforms to the tissue shape. This enables the enclosure of the tissue in the metamaterial and avoids the formation of air gaps between the metamaterial and the tissue which degrade the performance. The substrate may consist of one or more dielectric layers, where each of them attributes specific mechanical and practical properties to the whole structure and ensure ease of use and fabrication.

That is, in embodiments, each metamaterial layer comprises a first component arranged to support a periodic array of second components. In embodiments, the first component is non-rigid, optionally, flexible and/or stretchable. The first component may be elastic. The first component may be considered a substrate for the second component. In embodiments, the first component is a dielectric component and the second components are conducting components or, in other embodiments, the first component is a conducting component and the second components are dielectric components. In embodiments, the at least one dimension (that is less than the wavelength of the microwave signal) includes a dimension of at least one second component of the plurality of second components. In embodiments, the first component is a flexible dielectric such as a low surface energy polymer such as polydimethylsiloxane (PDMS) and polyimide, polyethylene naphthalene (PEN), polyethylene terephthalate (PET), polymethylmethacrylate (PMMA), and polystyrene.

Figure 15A:
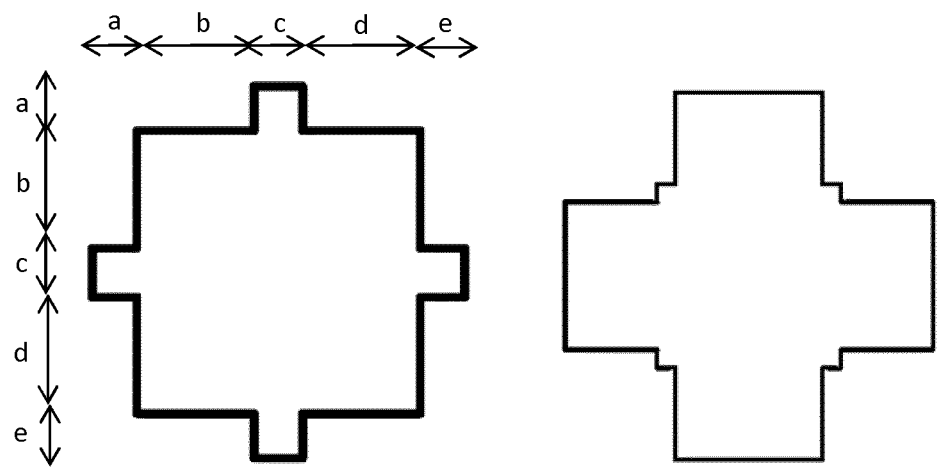
FIGS. 15a and 15b show cross-shape designs of metamaterial in accordance with embodiments.
Figure 15B:
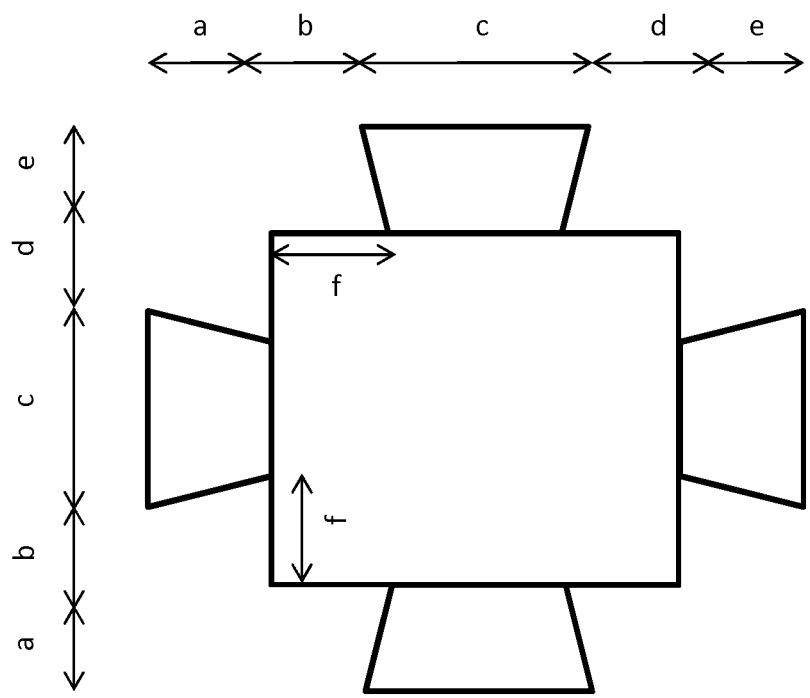
Figure 16:
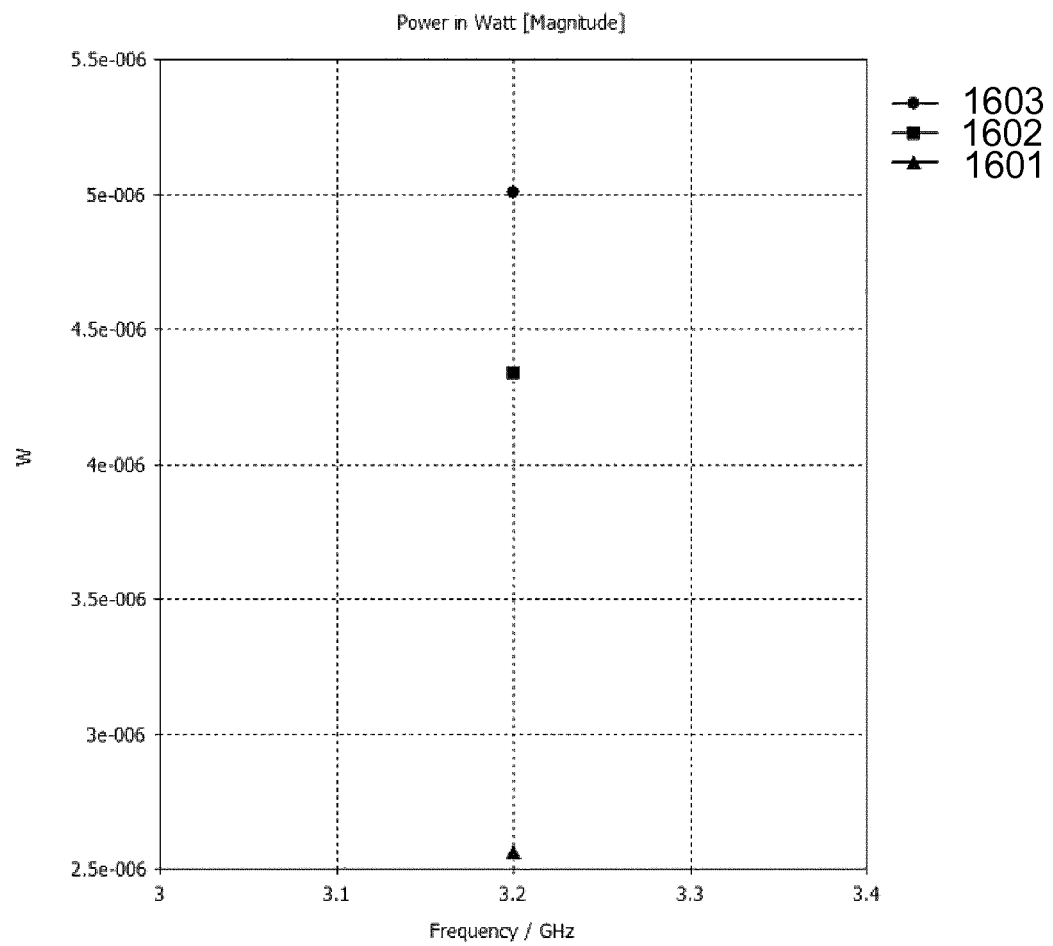
FIG. 16 plots energy absorption versus frequency for three configurations.

In embodiments, each second component comprises a quadrangular-shaped or cross-shaped component. Two alternative embodiments are presented in FIG. 13 which were designed on a cylindrical substrate. FIG. 15 shows a cross-shaped Jerusalem design for the metamaterial. The materials are copper printed on a dielectric substrate. The copper layer was printed on a substrate of 3 mm thickness. FIG. 16 shows the performance of the given embodiments versus the case of no metamaterial. Specifically, FIG. 16 shows energy absorption within the breast phantom. When the metamaterial design in accordance with embodiments is present, the energy is increased by up to 75%. The performance criterion used in the simulation results is the energy absorption in the breast phantom. FIG. 16 shows that by adding either design of the metamaterial the energy absorption in the phantom is increased by up to 75% at a specific frequency. Data point 1603 of FIG. 16 represents a first embodiment, data point 1602 represents a second embodiment and data point 1601 represents data obtained with no metamaterial. Finally, FIG.

17 shows an embodiment with the placement of the metamaterial in a cylindrical or ring setup.

The person skilled in the art will understand how to design a metamaterial for impedance matching with any particular biological material.

In a first example, the microwave radiation has a wavelength of 93 mm and the biological target is a female human breast. In this example, the metamaterial comprises a Rogers 5880 substrate and an array of copper elements, each element having a shape comprising the superposition of a quadrangle and cross (FIG. 15a). The dielectric substrate has a thickness of 3.175 mm. With reference to FIG. 15a, the size of each conducting element is: a=1.21 mm; b=8.04 mm; c=2.45 mm; d=8.04 mm; and e=1.21 mm. The conducing elements are spaced by 10.88 mm.

In embodiments, the first component is further arranged to support of periodic array of third components on the opposite side of the first component to the plurality of second components, wherein the at least one dimension is a dimension of at least one third component of the plurality of third components.

In a second example, the microwave radiation has a wavelength of 150 mm and the biological target is a human arm (brachium). In this example, the metamaterial comprises a Rogers 5880 substrate and an array of copper elements, each element having a shape comprising the superposition of a quadrangle and cross (FIG. 15b). The dielectric substrate has a thickness of 3.175 mm. With reference to FIG. 15b the size of each conducting element of the array is: a=4.7 mm; b=3.5 mm; c=8.05 mm; d=3.5 mm; e=4.7 mm; f=4.22 mm. The conducting elements of the array are spaced by 1.83 mm.

In embodiments, the conducting elements are coated or printed on the substrate by any appropriate technique which ensures adequate bonding. In other embodiments, the conducting elements are formed on the substrate by a photographic method.

It may therefore be understood that, in embodiments, each second component further comprises additional edges which have been added to the quadrangular-shaped or cross-shaped component. In some embodiments each second component has a shape comprising the superposition of a quadrangle and a cross.

System Hardware and Electronics

This component controls the feeding of the antenna array with the appropriate signals, and subsequently collects and records the received signals over an UWB range 0.8-4 GHz. It also interfaces with the software algorithms that reconstruct the tissue image information.

In embodiments, the system comprises:

1) The antenna subsystem, i.e. the array of microwave antenna elements;

2) A medium power RF multiplexer that will be able to route the RF transmission to any one of the array elements while the others will be set as receivers;

3) An RF ultra-wideband signal generator programmable to generate pulsed, swept or stepped frequency transmission signals;

4) A power amplifier that will increase the level of the transmitted signal to about 2 W (TBD);

5) A high dynamic range (about 100 dB) and low noise (2-4 dB) ultra-wideband RF receiver, including all the necessary front-end filters;

6) A high speed RF switch that will connect each receiving antenna, one at a time, to the input of the receiver;

7) For the case of pulsed transmitted signals, the output of the receiver will be directly sampled from a high-speed data converter system (at least 8 GSPS, 10 bits required);

8) For the case of swept or stepped frequency signals, a baseband down-converter synchronized with the signal generator can generate a baseband signal with small bandwidth that can be sampled with a low cost data converter system;

9) A mechanical system that will be able to rotate the antenna array and cover a hemispherical region of interest;

10) A synchronization subsystem that will synchronize the signal generator, multiplexer, switches, mechanical rotator and data acquisition;

11) A digital interface that will allow control, setup and reprogramming of every subsystem from the control station;

12) A built in self-test subsystem.

It may be readily understood that some of these features are optional and that some of these features are readily replaceable with equivalents.

In embodiments, the RF system comprises the following main subsystems: a) the RF Multiplexer b) the Transmitter c) The Receiver and d) the Processor System. A block diagram of the RF system in accordance with embodiments is shown in FIG. 16.

The RF Multiplexer connects one out of the 16 antennas to the output of the transmit path and any one of the remaining 15 antennas to the receive path input. It is controlled by the system firmware and remotely by the Software that has been especially designed for the system.

There is therefore provided a microwave imaging system comprising: the antenna system described above; a plurality of antennas each mounted in a respective antenna socket of the antenna mount; a microwave radiation source; and a multiplexer arranged to drive one antenna of the plurality of antennas to transmit a first microwave signal into the imaging chamber and drive at least two other antenna of the plurality of antennas to receive microwave radiation, in response to the first microwave signal, from the imaging chamber to form first microwave data related to the biological target. In embodiments, the first microwave signal has a frequency in the range 800 MHz to 4 GHz.

The microwave imaging system may further comprise: a motor; and a motor controller arranged to rotate the first housing by no more than 180 degrees, a synchronisation subsystem arranged such that, after rotation of the first housing, a second microwave signal is transmitted into the imaging chamber by one antenna of the plurality of antennas and at least two other antenna of the plurality of antennas receive microwave radiation, in response to the second microwave signal, from the imaging chamber to form second microwave data related to the biological target. In embodiments, the second microwave signal has a frequency in the range 800 MHz to 4 GHz.

In embodiments, the motor may also be configured to move up and down in the z-direction to create more "antenna rings". In embodiments, this configuration is used to provide a cylindrical imaging geometry (rather than a cup-shaped imaging geometry). In embodiments, the motor is further arranged to provide linear translation of the first housing.

The first microwave signal may have a different operating frequency to the second microwave signal. In embodiments, the multiplexer is arranged to alternately drive each antenna as a transmitter whilst the other antenna are driven as receivers to collect a plurality of microwave data related to the biological target. In further embodiments, the first housing is rotated between each transmission of a microwave signal, optionally, wherein the first housing is rotated between 0 to 90 degrees between each transmission of a microwave signal. In embodiments, at least one antenna of the plurality of antennas is an elliptical uni-planar antenna, optionally, operating at 1 to 4 GHz, further optionally, 1.5 to 3.4 GHz.

Figure 18:
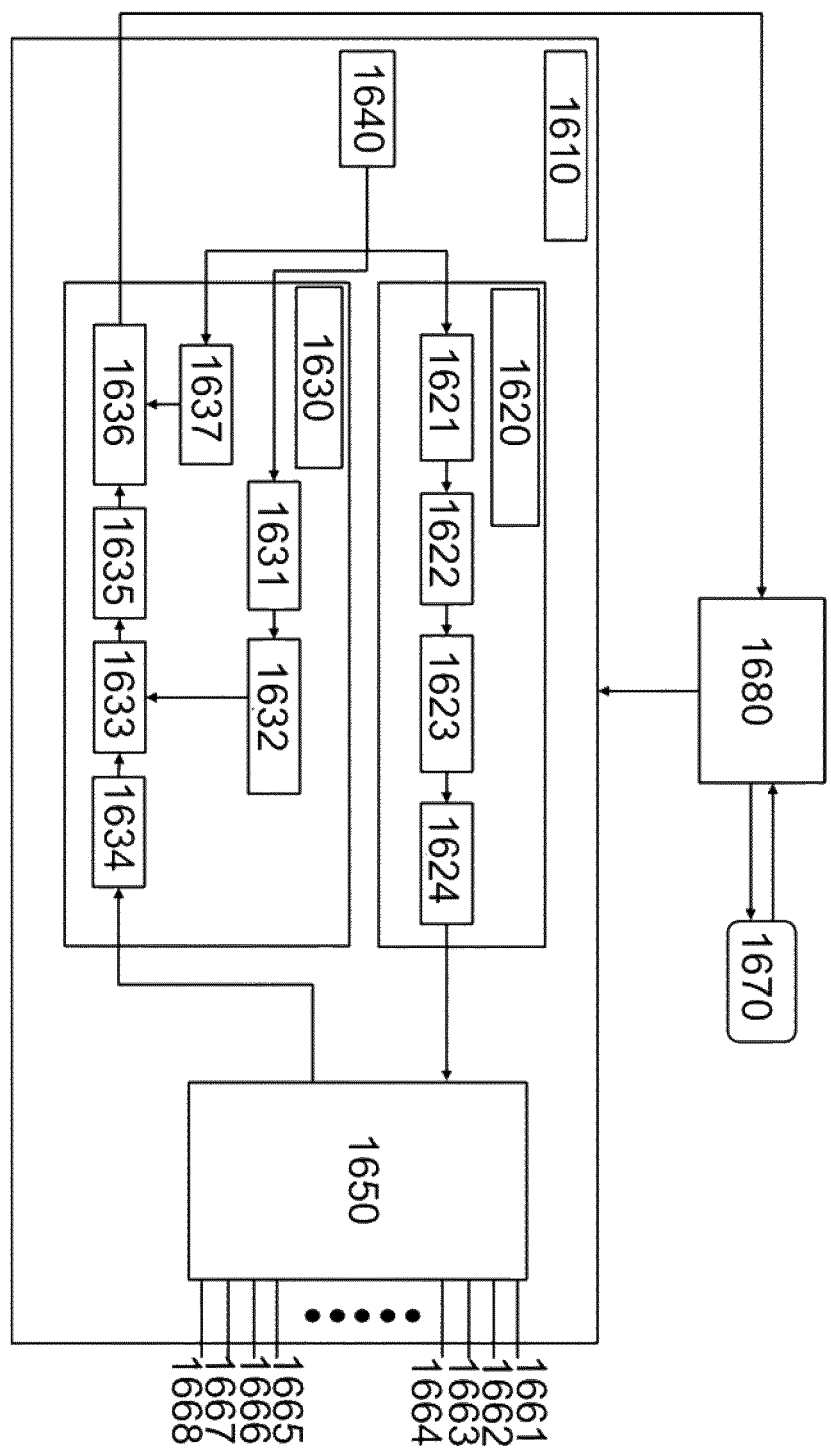
FIG. 18 is a block diagram of the RF system.

Specifically, FIG. 18 represents an RF transceiver 1610 comprising a RF transmitter 1620, RF receiver 1630 and RF multiplexer 1650. The RF transmitter 1620 comprises, in order, a Tx generator 1621, filter 1622, variable attenuator 1623 and Tx power amplifier 1624. The output of power amplifier 1624 is provided as the input to RF multiplexer 1650. The output of RF multiplexer 1650 is provided as an input to the RF receiver. The RF receiver 1630 comprises, in order, a Rx LNA 1634, mixer 1633, filter 1635 and IQ demodulator 1636. The output from RF receiver 1630 is provided as an input to a PC-controlled microprocessor 1680 which is in two-way communication with a user 1670. The PC-controlled microprocessor 1680 provides an input to the RF transceiver 1610. The RF transceiver 1610 further comprises a clock 1640 arranged to provide an input to: the Tx generator 1621; a first local oscillator 1637 of RF receiver 1630 which provides input to IQ demodulator 1636; and a second local oscillator 1631 of RF receiver 1610 which provides the input to a variable gain amplifier 1632 which, in turn, provides the input to mixer 1633. RF multiplexer 1650 is connected to a plurality of antennas 1661-1668.

The transmitter unit consists of the CLK Reference subsystem which is common for both transmit and receive paths, the RF Tx Generator, the Tx filter bank, the Tx Variable Attenuator and the Tx power amplifier which feeds the Tx signal to the RF multiplexer. The CLK reference is a highly stable clock generator which is used to provide the correct timing to all the subsystems of both Tx and Rx. Embodiments utilise a CLK that has a very low jitter performance, better than 5 psec. The CLK reference drives the RF Tx Generator which is comprised of an analog PLL-VCO. This PLL is computer controlled through a digital serial interface. This PLL has an integrated low phase noise Voltage Controlled Oscillator in it. The phase noise of this subsystem sets the ultimate sensitivity and discrimination of the receiver subsystem. The next subsystem is the Tx Filter Bank. This subsystem is needed in order to minimize the harmonics content from the previous subsystem (RF Tx Generator). The transmitter operates over a wide bandwidth 0.8-4 GHz, while the harmonic levels are in the range of −20 dBc to −10 dBc depending on the Tx operating frequency. In order to minimize these levels the Tx Filter bank includes three low-pass filters with corner frequencies at 1.2 GHz, 2.4 GHz and 3.9 GHz. These filters can be selected according to the Tx operating frequency band and provide at least 30 dB rejection to the harmonics generated by the RF Tx generator. In the filter bank the capability of bypassing the filters is also existent in case that the operator needs to operate the whole system in a wide open frequency bandwidth mode. Next the Tx Variable attenuator comprises of a low noise analog attenuator circuitry which provides at least 30 dBs of attenuation range. This power level flexibility is needed in order not to transmit excess power which will compress the receiver front-end. The power level transmitted is dependent on the location and the type of the investigated target. The Tx power amplifier subsystem is next transmitter's sub-module which is a two stage power amplifier design with at least 34 dB of gain over the whole frequency band 0.8-4 GHz. Finally the Transmit Path Antenna Multiplexer consists of several analog RF switches which provide the flexibility to make diverse combinations in between Tx and Rx antennas. The whole Antenna multiplexer is PC controlled and it makes any antenna to act as the transmitting element, while all the rest will be the receiving ones.

The Receiver system is comprised from the following subsystems: a) Receive Path Multiplexer b) YIG Preselection Filter, c) Rx LNA, d) First Mixer, e) 1st LO generator, f) Second LO generator, g) IQ demodulator.

The Receive path multiplexer is the same as the TX path multiplexer. The RF receiver front-ends are vulnerable to unwanted transmissions/reflections. These unwanted signals limit the sensitivity of a receiver system. In order to prevent such a situation in MiSCAN system which is designed to have a very good low noise performance a YIG tuned bandpass filter is incorporated. The filter has a typical instantaneous bandwidth of 15 MHz and it can be tuned over the whole RF frequency bandwidth of 0.8-4 GHz. Typical insertion loss of this filter is 2 dB only and its selectivity corresponds to a 7th order Chebyshev type filter.

The receiver architecture is a super-heterodyne one, so two stages of frequency translation take place. The First Mixer subsystem down-converts the RF received signal to an intermediate frequency. Before doing that a cascade of low noise amplifiers amplify the received signal by at least 30 dB. The down-conversion mixer is highly linear in order to prevent as much as possible any intermodulation issues and thus increased harmonics content which will limit the discrimination of the wanted received signal from the intermodulation products. The IF signal is band limited using surface acoustic wave bandpass filters which provide ultimate selectivity. The first local oscillator is based on the same PLL-VCO chip of the RF Tx generator. It is driven from the same clock generator as in the transmitter case in order to have phase coherency. The RF output of the first local oscillator is used to drive the local oscillator port of the mixer of the First Mixer subsystem. The second Local Oscillator subsystem is using also the same PLL-VCO chip as in the First Local Oscillator subsystem. It is also phase coherent to the previous frequency generators. The RF output of this system is used to provide local oscillator drive to the IQ demodulator subsystem of the baseband.

The IQ demodulation is implemented using a low noise high sensitivity IQ demodulator chip. This chip is a wideband IQ demodulator with integrated voltage variable RF amplifier, baseband voltage gain amplifiers for the IQ signals and an integrated hybrid coupler functionality system in order to produce internally the 0/90 degrees local oscillator phase difference needed for the proper IQ demodulator performance. The IQ demodulator is driven with phase coherency with respect to the transmitted signal. Phase coherency is of crucial importance in order to properly demodulate the baseband "I" and "Q" signals which will be produced from the mixing of the Tx transmitted RF signal and the Rx received RF signal from the target reflection.

The uP system consists of a high end microprocessor running at 80 MHz and a set of peripheral chips (EEPROM, FLASH, Communications transceiver, D/A converters, real Time Clock, YIG Filter Driver etc.). Internally the uP has a rich set of peripherals, needed for the implementation of the motion functions and network communications. The system is connected to an Adhoc network via an RS485 transceiver. A simple 2-wire cable is needed to connect the board to the computer driver software. The system firmware implements all the functions needed for the Configuration of the CPU, implementation of the AMS Link, handling of the commands from the Software Device Driver, and controlling the motion system. Especially designed firmware Libraries is the general tool to implement firmware for the other systems.

The Imaging Algorithm

It may be readily understood that, in embodiments, there is provided a processor arranged to perform microwave tomography of the biological target based on received microwave data and, optionally, image healthy or malignant cancer tissue, a bone, an internal blood trauma region or cartilage.

Quantitative microwave imaging for medical applications estimates the spatial distribution of dielectric properties in a tissue region by solving an electromagnetic (EM) inverse scattering problem. In microwave tomography, an array of antennas surrounds the region of interest inside the patient's human body. The scattered energy is recorded by the array and the EM inverse scattering algorithm processes the signals to form an image of the probed region by solving a non-linear inverse problem which reconstructs the complex permittivity of the interrogated tissue.

Microwave imaging methods for medical diagnosis typically require effective solutions to inverse scattering problems. In particular, two major strategies are employed for the solution of MWI problems; the first is based on certain approximations that lead to the linearization of the inverse problem. An example of a linear approach is diffraction tomography, which has been applied to many practical problems where the underlying simplifying assumptions (such as the Born approximation) are valid. The second family of methods aims to develop iterative algorithms based on numerical optimization techniques. Multiple scattering effects are to some extent taken into account by these iterative algorithms, offering resolution possibilities beyond the diffraction limit. A great challenge in most inverse scattering problems is caused by limitations in data acquisition due to cost or other practical issues. As a result, the number of (known) data points in most cases is much smaller than the number of (unknown) reconstruction points, causing the nonlinear inverse scattering problems to be ill-posed. Regularization schemes employed to tackle this problem typically result in suppression of high frequency data, reducing significantly the resolution capabilities of MWI systems.

The proposed imaging system focuses on microwave tomography algorithms based on the Distorted Born Iterative Method (DBIM), which is described by an integral equation:

$$E^{sc}(r)=E^t(r)-E^b(r)=\omega^2\mu\int_r dr' \overline{G}^b(r,r')\Delta\epsilon(r')E^b(r')$$

where $E^{sc}$ and $E^t$ are the scattered and total electric fields, $E^b$ is the incident field in the presence of the background permittivity (background field), $G^b$ is the dyadic Green's function for the background, and $\Delta\epsilon(r)$ is the unknown permittivity to be reconstructed.

As equivalent to applying Gauss-Newton optimization to EM inverse scattering, the DBIM approximates the non-linear inverse scattering problem with a set of linear equations at each DBIM iteration. The resulting linear problem is typically under-determined and computationally demanding, and its fast and accurate solution is critical for the DBIM convergence to a realistic estimate of the unknown profiles. Moreover, the solution of this inverse problem is sensitive to measurement noise and depends on a priori information about the imaging domain, which is used as "initial guess" for the iterative algorithm. Therefore, special techniques must be applied to improve the stability of the algorithms and the resolution in the resulting images.

To this end, the imaging algorithm employed by the inventors uses several techniques to improve imaging performance in an innovative manner:

The forward solver used at each iteration of the algorithm is based on a GPU implementation of the FDTD method. The implementation is based on the CUDA programming language, and results in 60 times faster computations than a non-GPU version of the code. This feature of the system enables two-dimensional images in real time an also permits three-dimensional imaging in less than 24 hours.

A two-step iterative shrinkage/thresholding (TwIST) algorithm is applied for the first time to solve the linear inverse problem at each iteration [5]. Relative to conventional algorithms, the TwIST exhibits much faster convergence rate and leads to more robust solutions to ill-conditioned problems. The algorithm can be mathematically described by the equation, $$\Delta\chi_{k+1}=(1-\alpha)\Delta\chi_{k-1}+(\alpha-\beta)\Delta\chi_k+\beta\Psi_\lambda(\Delta\chi_k+A^*(y-A\Delta\chi_k))$$

where the parameters $\alpha$ and $\beta$ depend on the problem at hand. These and other parameters of the TwIST algorithm are carefully optimized in a unique manner for application to the proposed imaging system via the DBIM approach.

Multiple frequency data in the range from 1.0-4.0 GHz is used with the DBIM algorithm, in order to improve resolution beyond current state-of-the-art microwave tomography systems, which consider frequencies beyond 2 GHz to guarantee stability. On the contrary, the proposed algorithm guarantees stability by dividing the inversion process in two steps. The first step assumes a homogenous tissue model in order to estimate its average properties more accurately, and uses low-frequency data at 1 GHz to find a low-resolution solution to the inverse problem. The second step emphasizes higher resolution details by using data up to 4.0 GHz. This two-step process is a unique way of combining stable convergence to the optimal solution (first step) with enhanced resolution due to high-frequency data (second step).

The algorithm also allows reconstruction by projection onto a wavelet basis. Projection onto wavelets combined with iterative-shrinkage algorithms is proposed for the first time for an experimental imaging system.

In embodiments, the processor is arranged to: process microwave data received in response to transmitted microwave signals in the range 800 MHz to 1.5 GHz using a first iterative Gauss-Newton algorithm; and process microwave data received in response to transmitted microwave signals in the range 1.5 to 4 GHz using a second iterative Gauss-Newton algorithm, wherein the input to the second iterative Gauss-Newton algorithm is the output of the first iterative Gauss-Newton algorithm and the output of the second iterative Gauss-Newton algorithm is a quantitative tomographic image of the biological target. Optionally, the input to the first iterative Gauss-Newton algorithm does not include prior knowledge related to the material properties of the biological target.

In embodiments, the system is arranged to receive data related to the geometry, size and/or shape of each housing and determine parameters of the first and/or second iterative Gauss-Newton algorithm based on the data related to the geometry, size and/or shape of each housing. In embodiments, the data related to the geometry, size and/or shape of each housing is scan-designed-print data.

In advantageous embodiment, the software system takes advantage of a Graphics Processing Unit, "GPU", which can accelerate processing of the first and second iterative algorithms. That is, in embodiment, the system comprises a GPU arranged to process the first and second iterative algorithms.

To evaluate these techniques, numerical simulations have been performed with a breast phantom surrounded by multiple dipole antennas. The simulations are two-dimensional (2-D), based on axial breast models taken from UW-Madison's repository of 3-D MRI-derived numerical breast phantoms. Each 2-D test phantom is surrounded by a cylindrical array of 16 evenly-spaced line sources.

In our 2-D tests, an FDTD solver on uniform grid cell is used as the forward solver at each iteration of the DBIM algorithm. The algorithm estimates the parameters ε∞, εS, and σs of the Debye model for the complex relative permittivity, $$\epsilon_r(\omega) = \epsilon_\infty + \frac{\epsilon_s - \epsilon_\infty}{1 + j\omega\tau} - j\frac{\sigma_s}{\omega\epsilon_0}$$

where τ is assumed constant for all tissues. To compare with previous implementations, the same background medium of lossless dielectric with $\epsilon_r$=2.6 is considered in all our simulation testbeds, and the Debye parameters for the various tissues are extracted from UW-Madison's repository data.

Figure 17:
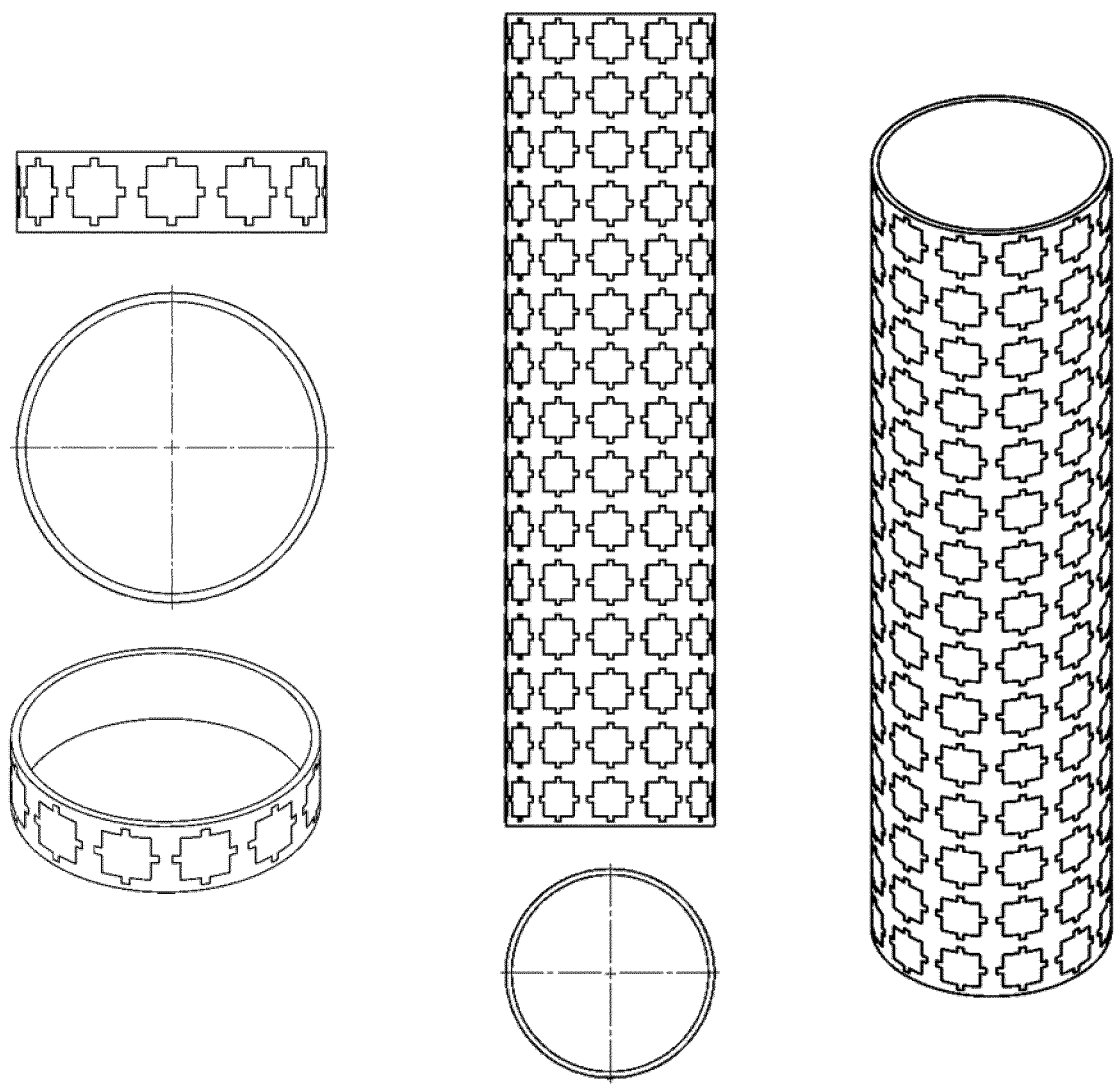
FIG. 17 shows a cylindrical metamaterial.
Figure 19:
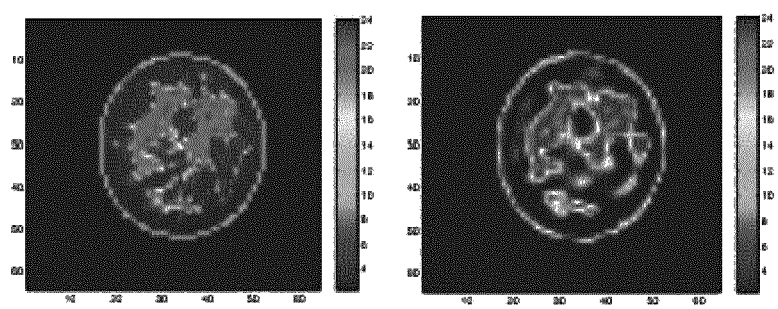
FIG. 19 shows quantitative images of the (a) true and (b) reconstructed breast tissue composition formed in accordance with embodiments.

The superior performance of the inventors' implementation of the DBIM approach is demonstrated in FIG. 19, which features unprecedented resolution capabilities. The algorithm manages to recover the breast structure with a level of detail that is comparable to the original 2 mm-voxel image. The reconstructed image estimates very accurately the breast tissue composition and the skin properties and thickness, and also recovers the 1-cm diameter tumour that is artificially introduced as a sphere on the right side of the breast. These images can only be obtained with the two-step procedure described previously, which allows a stable low-frequency (1 GHz) reconstruction at the end of the first step, which is then used as the input estimate (the "initial guess") for the multiple-frequency second step reconstruction. We note that the distribution of one of the Debye parameters (ε∞) is plotted in FIG. 17, but similar quality is obtained for the other two Debye parameters (in this figure, (a) plots the true and (b) the reconstructed spatial breast tissue composition using the proposed algorithm).

Although aspects and embodiments have been described above, variations can be made without departing from the inventive concepts disclosed herein.

The invention claimed is:

1. A microwave imaging system comprising:
   an antenna system comprising:
      a plurality of antennas;
      an antenna mount comprising a housing at least partially defining an imaging chamber for receiving a biological target, wherein the housing comprises a plurality of antenna sockets, wherein each respective antenna of the plurality of antennas is received and mounted in a respective antenna socket of the plurality of antenna sockets such that each respective antenna is directed into the imaging chamber; and
      a metamaterial coupled to an internal wall of the imaging chamber, wherein the metamaterial is non-rigid so as to substantially conform to a shape of the internal wall of the imaging chamber;
   a microwave radiation source configured to generate transmission signals;
   a multiplexer arranged to:
      select one antenna of the plurality of antennas as a transmit antenna and route the transmission signals to the transmit antenna, thereby driving the transmit antenna to transmit a plurality of microwave signals into the imaging chamber, and
      select at least two other antennas of the plurality of antennas to receive microwave radiation, in response to the transmitted plurality of microwave signals, from the imaging chamber to form a plurality of microwave data related to the biological target; and
   a processor arranged to perform microwave tomography of the biological target based on the received plurality of microwave data, wherein the processor is configured to:
      control the microwave radiation source, the multiplexer, and the antenna system to transmit first microwave signals, of the plurality of microwave signals, into the imaging chamber and receive first microwave data, of the plurality of microwave data, in response thereto, wherein the first microwave signals are in the frequency range of 800 MHz to 1.5 GHz;
      process the first microwave data using a first iterative Gauss-Newton algorithm;
      control the microwave radiation source, the multiplexer, and the antenna system to transmit second microwave signals, of the plurality of microwave signals, into the imaging chamber and receive second microwave data, of the plurality of microwave data, in response thereto, wherein the second microwave signals are in the frequency range of 1.5 GHz to 4 GHz;
      process the second microwave data using a second iterative Gauss-Newton algorithm, wherein an input to the second iterative Gauss-Newton algorithm is an output of the first iterative Gauss-Newton algorithm and an output of the second iterative Gauss-Newton algorithm is a quantitative tomographic image of the biological target.

2. The microwave imaging system of claim 1, wherein the processor is arranged to receive data related to a geometry, a size and/or a shape of the housing and determine parameters of the first iterative Gauss-Newton algorithm and/or parameters of the second iterative Gauss-Newton algorithm based on the data related to the geometry, the size and/or the shape of the housing.

3. The microwave imaging system of claim 1, further comprising a Graphics Processing Unit (GPU) arranged to process the first and the second iterative Gauss-Newton algorithms.

4. The microwave imaging system of claim 1, wherein the plurality of microwave signals has a frequency in the range 800 MHz to 4 GHz.

5. The microwave imaging system of claim 1, wherein the housing is non-rigid so as to be conformable to a shape of the biological target.

6. The microwave imaging system of claim 1, wherein the metamaterial comprises at least one metamaterial layer arranged to line the internal wall of the imaging chamber.

7. The microwave imaging system of claim 6, wherein each metamaterial layer has at least one dimension less than a wavelength of the plurality of microwave signals.

8. The microwave imaging system of claim 7, wherein the at least one dimension includes a respective thickness of each metamaterial layer.

9. The microwave imaging system of claim 7, wherein each metamaterial layer comprises a first component and a periodic array of second components supported by the first component.

10. The microwave imaging system of claim 9, wherein the first component is non-rigid.

11. The microwave imaging system of claim 9, wherein:
the first component is a dielectric component and the second components are conducting components; or
the first component is a conducting component and the second components are dielectric components.

12. The microwave imaging system of claim 11, wherein the at least one dimension includes a dimension of at least one second component of the periodic array of second components.

13. The microwave imaging system of claim 9, wherein each second component comprises a quadrangular-shaped or cross-shaped component.

14. The microwave imaging system of claim 13, wherein each second component further comprises additional edges which have been added to the quadrangular-shaped or cross-shaped component.

15. The microwave imaging system of claim 9, wherein each second component has a shape comprising a superposition of a quadrangle and a cross.

16. The microwave imaging system of claim 15, wherein the metamaterial comprises a photoconducting material.

17. The microwave imaging system of claim 9, wherein each metamaterial layer further comprises a periodic array of third components, wherein the first component comprises a first side and a second side opposite the first side, wherein the first component is arranged to support the periodic array of second components on the first side of the first component, and wherein the first component is further arranged to support the periodic array of third components on the second side of the first component, wherein the at least one dimension is a dimension of at least one third component of the periodic array of third components.

18. The microwave imaging system of claim 1, wherein the metamaterial has a dynamically tunable operating frequency.

19. The microwave imaging system of claim 1, wherein the housing is a substantially spherical, hemispherical or parallelepiped shell and the imaging chamber is an internal volume of the shell.

20. The microwave imaging system of claim 1, wherein the housing is arranged to rotate around the imaging chamber.

21. The microwave imaging system of claim 1, wherein:
the plurality of antennas is divided into a first group of antennas and a second group of antennas;
the housing is divided into a first housing and a second housing, wherein each of the first housing and the second housing at least partially defines a respective portion of the imaging chamber;
the plurality of antenna sockets is divided into a first group of antenna sockets and a second group of antenna sockets, wherein the first housing comprises the first group of antenna sockets and the second housing comprises the second group of antenna sockets;
each respective antenna of the first group of antennas is received and mounted in a respective antenna socket of the first group of antenna sockets such that each respective antenna of the first group of antennas is directed into the imaging chamber;
each respective antenna of the second group of antennas is received and mounted in a respective antenna socket of the second group of antenna sockets such that each respective antenna of the second group of antennas is directed into the imaging chamber; and
the second housing is arranged to rotate around the imaging chamber.

22. The microwave imaging system of claim 21, wherein the first housing and the second housing collectively form a substantially spherical, hemispherical or planar shell and the imaging chamber is an internal volume of the shell.

23. The microwave imaging system of claim 21, wherein the second housing is rotatably-coupled to the first housing.

24. The microwave imaging system of claim 21, wherein each of the first housing and the second housing comprises suction holes arranged to couple with a suction system for removing air from the imaging chamber.

25. The microwave imaging system of claim 1, wherein the metamaterial is perforated.

26. A method for microwave imaging a biological target, the method comprising:
providing a microwave imaging system according to claim 1;
driving the selected one antenna of the plurality of antennas with the transmission signals from the microwave radiation source to transmit the plurality of microwave signals into the imaging chamber; and
receiving, at the selected at least two other antennas, the microwave radiation in response to the transmitted plurality of microwave signals, from the imaging chamber to form the plurality of microwave data related to the biological target.

* * * * *